US006783972B1

(12) United States Patent
Byrne et al.

(10) Patent No.: US 6,783,972 B1
(45) Date of Patent: Aug. 31, 2004

(54) METHODS FOR LARGE-SCALE PRODUCTION OF RECOMBINANT AAV VECTORS

(75) Inventors: Barry J. Byrne, Gainesville, FL (US); James E. Conway, Elkton, MD (US); Gary S. Hayward, Towson, MD (US); Nicholas Muzyzcka, Gainesville, FL (US); Sergei Zolotukhin, Gainesville, FL (US)

(73) Assignee: University of Florida Research Foundation, Gainesville, FL (US)

( * ) Notice: Subject to any disclaimer, the term of this patent is extended or adjusted under 35 U.S.C. 154(b) by 0 days.

(21) Appl. No.: 09/404,448

(22) Filed: Sep. 22, 1999

Related U.S. Application Data
(60) Provisional application No. 60/101,507, filed on Sep. 22, 1998.

(51) Int. Cl.$^7$ .......................... C12N 7/01; C12N 15/09; C12N 15/00; C12P 21/06; C07H 21/04
(52) U.S. Cl. ............................ 435/235.1; 435/320.1; 435/325; 435/456; 435/69.1; 536/23.1; 514/44
(58) Field of Search ............................ 435/325, 235.1, 435/320.1, 456, 69.1; 536/23.1; 514/44

(56) References Cited

U.S. PATENT DOCUMENTS

| | | | |
|---|---|---|---|
| 5,173,414 A | 12/1992 | Lebkowski et al. | 435/172.3 |
| 5,354,678 A | 10/1994 | Lebkowski et al. | 435/172.3 |
| 5,589,377 A | 12/1996 | Lebkowski et al. | 435/240.2 |
| 5,661,033 A | 8/1997 | Ho et al. | 435/320.1 |
| 5,693,531 A * | 12/1997 | Chiorini et al. | 435/325 |
| 5,780,280 A | 7/1998 | Lebkowski et al. | 435/172.3 |
| 5,846,707 A | 12/1998 | Roizman | 435/5 |
| 5,869,305 A | 2/1999 | Samulski et al. | 435/172.3 |
| 5,879,934 A | 3/1999 | DeLuca | 435/320.1 |
| 5,928,913 A * | 7/1999 | Efstathiou et al. | 435/172.3 |
| 5,945,335 A | 8/1999 | Colosi | 435/369 |
| 5,998,174 A * | 12/1999 | Glorioso et al. | 435/91.4 |

FOREIGN PATENT DOCUMENTS

| | | | |
|---|---|---|---|
| WO | WO 95/06743 | 3/1995 | |
| WO | WO 95/06743 A2 * | 3/1995 | 435/320.1 |
| WO | WO 97/20935 | 6/1997 | |
| WO | WO 99/20778 | 4/1999 | |

OTHER PUBLICATIONS

Stephen A. Rice et al, Genetic Evidence for Two Distinct Transactivation Functions of the Herpes Simplex Virus & Protein ICP27, Journal of Virology, Apr. 1990, pp 1704–1715.*
Nicholas Muzyczka et al, In vitro replication of adeno–associated virus DNA, seminars in Virology, vol. 2, 1991: pp 281–290.*
Buller, "Herpes simplex virus types 1 and 2 completely help adenovirus–associated virus replication," *J. Virol.* 40:241–247, 1981.
Conway et al., "Recombinant adeno–associated virus type 2 replication and packaging is entirely supported by a herpes simplex virus type I amplicon expressing Rep and Cap," *J. Virol.* 71:8780–8789, 1997.

Heilbronn et al., "The adeno–associated virus rep gene suppresses herpes simplex virus–induced DNA amplification," *J. Virol.* 64:3012–3018, 1990.
Johnston et al., "HSV/AAV hybrid amplicon vectors extend transgene expression in human glioma cells," *Hum. Gene Ther.* 8:359–370, 1997.
Mishra and Rose, "Adeno–associated virus DNA replication is induced by genes that are essential for HSV–1 DNA synthesis," *Virology* 179:632–639, 1990.
Rose and Koczot, "Adenovirus–associated virus multiplication VII. Helper requirement for viral deoxyribonucleic acid and ribonucleic acid synthesis," *J. Virol.* 10:1–8, 1972.
Thomson et al., "Acquisition of the human adeno–associated virus type–2 rep gene by human herpesvirus type–6," *Nature* 351:78–80, 1991.
Thomson et al., "Human herpesvirus 6 (HHV–6) is a helper virus for adeno–associated virus type 2 (AAV–2) and the AAV–2 rep gene homologue in HHV–6 can mediate AAV–2 DNA replication and regulate gene expression," *Virology* 204:304–311, 1994.
Weindler and Heilbronn, "A subset of herpes simplex virus replication genes provides helper functions for productive adeno–associated virus replication," *J. Virol.* 65:2476–2483, 1991.
Conway et al., "High–titer recombinant adeno–associated virus production utilizing a recombinant herpes simplex virus type I vector expressing AAV–2 Rep and Cap," *Gene Therapy,* 6(6):986–993, 1999.
Database WPI, Section Ch, Week 199933, Derwent Publications Ltd., London, GB; AN 1999–386309, XP002136602 & CN 1 213 699 A (Inst Birology China Prevention Medical A), Apr. 14, 1999, abstract.
International Search Report mailed May 17, 2000 (PCT/US99/22052; 4300.012110).
Vincent et al., "Analysis of recombinant adeno–associated virus packaging and requirements for rep and cap gene products," *J. Virol.,* 71(3):1897–1905, 1997.
Yuelong et al., "A novel recombinant adeno–associated virus vector packaging system with HSV–1, amplicon providing helper functions," *Science in china Series C Life Sciences,* 43:465–470, 1999, Abstract only.
Zhang et al., "High–titer recombinant adeno–associated virus production from replicating amplicons and herpes vectors deleted for glycoprotein H," *Hum. Gene Ther.,* 10:2527–2537, 1999.
Feudner et al., "Optimization of recombinant adeno–associated virus production using an herpes simplex virus amplicon system," *J. Virol. Meth.,* 96:97–105, 2001.

* cited by examiner

*Primary Examiner*—Gerry Leffers
(74) *Attorney, Agent, or Firm*—Edwards & Angell, LLP

(57) ABSTRACT

Disclosed are HSV-1 amplicons that supply all necessary helper functions required for rAAV packaging and methods for their use. These HSV-1 amplicons have been shown to be capable of rescuing and replicating all forms of rAAV genomes including rAAV genomes introduced into cells by infection of rAAV virions, rAAV genomes transfected into cells on plasmids or proviral rAAV genomes integrated into cellular chromosomal DNA. Also provided are methods for preparing high-titer rAAV vector compositions suitable for gene therapy and the delivery of exogenous polynucleotides to selected host cells.

8 Claims, 4 Drawing Sheets

Figure 1:
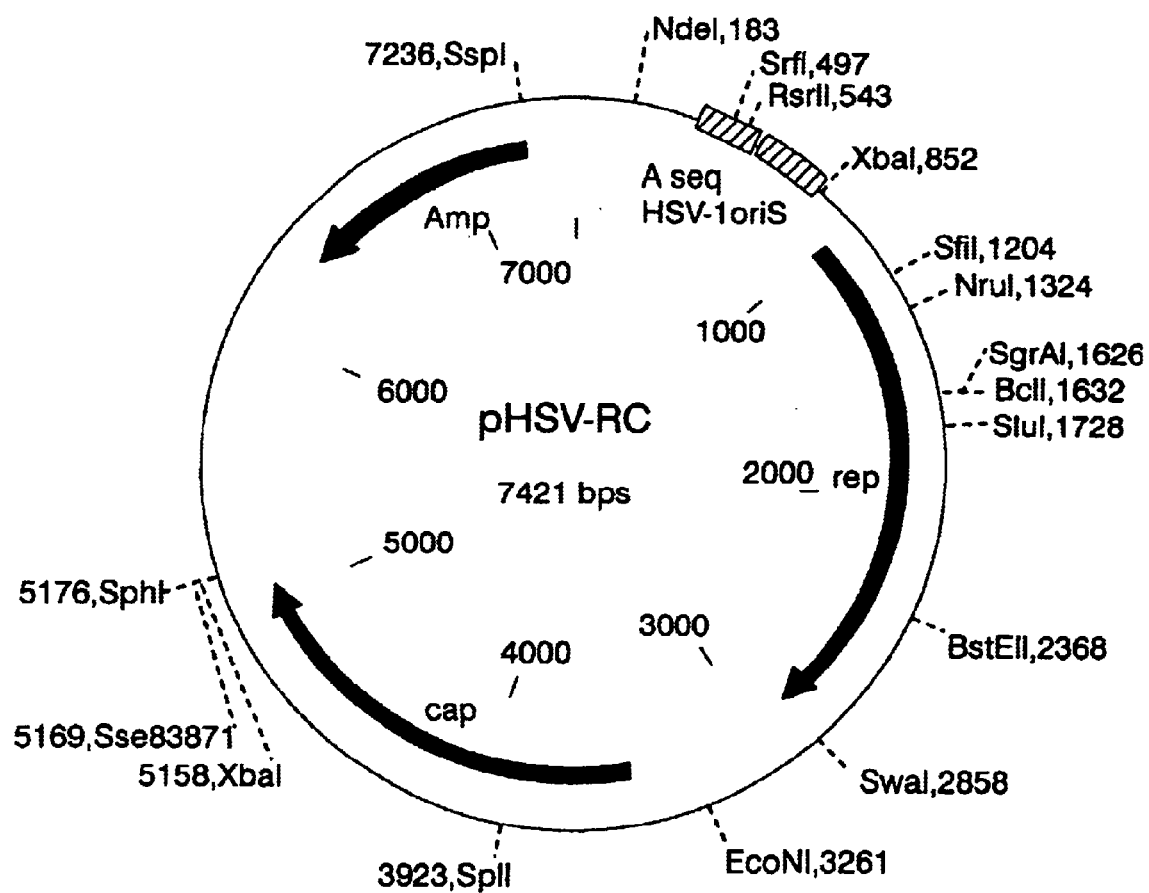

Rescue of rUF2 From Proviral Cell Line GFP92

METHODS FOR LARGE-SCALE PRODUCTION OF RECOMBINANT AAV VECTORS

The present application claims the priority date of co-pending provisional application Serial No. 60/101,507, filed Sep. 22, 1998 now abandoned, the entire disclosure of which is incorporated herein by reference without disclaimer.

The United States government has rights in the present invention pursuant to grant numbers CA28473 and CA09243 from the National Institutes of Health.

1.0 BACKGROUND OF THE INVENTION

1.1 Field of the Invention

The present invention relates generally to the field of molecular biology. More particularly, it concerns the replication and packaging of recombinant adeno-associated viral-based vectors, and a scaleable process for their large-scale production.

1.2 Description of Related Art 1.2.1 Adeno-associated Virus

Adeno-associated virus-2 (AAV)-2 is a human parvovirus that can be propagated both as a lytic virus and as a provirus (Cukor et al., 1984; Hoggan et al., 1972). The viral genome consists of linear single-stranded DNA (Rose et al., 1969), 4679 bases long (Srivastava et al., 1983), flanked by inverted terminal repeats of 145 bases (Lusby and Berns, 1982). For lytic growth AAV requires co-infection with a helper virus. Either adenovirus (Ad; Atchinson et al., 1965; Hoggan, 1965; Parks et al., 1967) or herpes simplex virus (HSV; Buller et al., 1981) can supply the requisite helper functions. Without helper, there is no evidence of AAV-specific replication or gene expression (Rose and Koczot, 1972; Carter et al., 1983). When no helper is available, AAV persists as an integrated provirus (Hoggan, 1965; Berns et al., 1975; Handa et al., 1977; Cheung et al., 1980; Berns et al., 1982).

Integration apparently involves recombination between AAV termini and host sequences and most of the AAV sequences remain intact in the provirus. The ability of AAV to integrate into host DNA is apparently an inherent strategy for insuring the survival of AAV sequences in the absence of the helper virus. When cells carrying an AAV provirus are subsequently superinfected with a helper, the integrated AAV genome is rescued and a productive lytic cycle occurs (Hoggan, 1965).

AAV sequences cloned into prokaryotic plasmids are infectious (Samulski et al., 1982). For example, when the wild type AAV/pBR322 plasmid, pSM620, is transfected into human cells in the presence of adenovirus, the AAV sequences are rescued from the plasmid and a normal AAV lytic cycle ensues (Samulski et al., 1982). This renders it possible to modify the AAV sequences in the recombinant plasmid and, then, to grow a viral stock of the mutant by transfecting the plasmid into human cells (Samulski et al., 1983; Hermonat and Muzyczka, 1984).

AAV contains at least three phenotypically distinct regions (Hermonat and Muzyczka, 1984). The rep region codes for one or more proteins that are required for DNA replication and for rescue from the recombinant plasmid, while the cap and lip regions appear to code for AAV capsid proteins and mutants within these regions are capable of DNA replication (Hermonat and Muzyczka, 1984). It has been shown that the AAV termini are required for DNA replication (Samulski et al., 1983).

The construction of two *E. coli* hybrid plasmids, each of which contains the entire DNA genome of AAV, and the transfection of the recombinant DNAs into human cell lines in the presence of helper adenovirus to successfully rescue and replicate the AAV genome has been described (Laughlin et al., 1983; Tratschin et al., 1984a; 1984b).

1.2.2 rAAV Vectors as Vehicles for Gene Therapy

Recombinant adeno-associated virus (rAAV) vectors have important utility as vehicles for the in vivo delivery of polynucleotides to target host cells (Kessler et al., 1996; Koeberl et al., 1997; Kotin, 1994; Xiao et al., 1996). rAAV vectors are useful vector for efficient and long-term gene transfer in a variety of mammalian tissues, e.g., lung (Flotte, 1993), muscle (Kessler, 1996; Xiao et al., 1996; Clark et al., 1997; Fisher et al., 1997), brain (Kaplitt, 1994; Klein, 1998) retina (Flannery, 1997; Lewin et al., 1998), and liver (Snyder, 1997).

It has also been shown that rAAV can evade the immune response of the host by failing to transduce dendritic cells (Jooss et al., 1998). Clinical trials have been initiated for several important mammalian diseases including hemophilia B, muscular dystrophy and cystic fibrosis (Flotte et al., 1996; Wagner et al., 1998).

1.2.3 Contemporary Methods for Preparing rAAV Vectors

Currently, rAAV is most often produced by co-transfection of rAAV vector plasmid and wt AAV helper plasmid into Ad-infected 293 cells (Hermonat and Muzyczka, 1984). Recent improvements in AAV helper design (Li et al., 1997) as well as construction of non-infectious mini-Ad plasmid helper (Grimm et al., 1998; Xiao et al., 1998; Salvetti, 1998) have eliminated the need for Ad infection, and made it possible to increase the yield of rAAV up to $10^5$ particles per transfected cell in a crude lysate. Scalable methods of rAAV production that do not rely on DNA transfection have also been developed (Chiorini et al., 1995; Inoue and Russell, 1998; Clark et al., 1995). These methods, which generally involve the construction of producer cell lines and helper virus infection, are suitable for high-volume production.

The conventional protocol for downstream purification of rAAV involves the stepwise precipitation of rAAV using ammonium sulfate, followed by two or preferably, three rounds of CsCl density gradient centrifugation. Each round of CsCl centrifugation involves fractionation of the gradient and probing fractions for rAAV by dot-blot hybridization or by PCR™ analysis.

1.3 Deficiencies in the Prior Art

A major problem associated with the use of rAAV vectors has been the difficulty in producing large quantities of high-titer vector stocks (Clark et al., 1995, Clark et al., 1996). The standard production protocol involves low-efficiency transfection of plasmid DNA containing the rep and cap genes and a plasmid containing the rAAV provirus with inverted terminal repeats. Cells are then superinfected with adenovirus to provide essential helper functions required for rAAV production.

Alternative procedures have been developed to improve the efficiency of rAAV production by delivering rep, cap and the adenovirus helper genes. These technologies have included the generation of rep and cap inducible cell lines and plasmids expressing the essential adenovis helper genes (Clark et al., 1995; Clark et al., 1996; Vincent et al., 1990; Xiao et al., 1998; Grimm et al., 1998). Although these techniques have improved the yield of rAAV production, they have not been entirely satisfactory. Procedures employing transfection methods are not efficient, and tend to be extremely variable in yield from preparation to preparation. Moreover, such procedures are difficult to scale up to produce the large quantity of rAAV vector needed for clinical trials.

The production of rep and cap inducible cell lines is a particular challenge because the yield of rAAV produced from different clones is variable and does not exceed the efficiency of transfection methods (Clark et al., 1995; Clark et al., 1996, Vincent et al., 1990). Production procedures for rAAV that utilize adenovirus and transfection of rep and cap containing plasmids have the potential to generate wild type AAV (wt AAV) through illegitimate recombination of the ITRs with rep and cap sequences. This leads to preferential amplification of the wt AAV genome over the rAAV genome.

A major drawback in the use of rAAV vectors for gene transfer studies in vivo and their application to clinical procedures, such as that of gene therapy, has been the difficulty in producing large quantities of rAAV vector. For the therapeutic correction of some diseases, it is estimated that $1 \times 10^{14}$ rAAV particles must be administered per patient. This will require the culture of greater than $1 \times 10^{12}$ cells to produce the quantity of rAAV vector that will be needed to therapeutically treat each patient. The use of contemporary transfection methods on this scale of rAAV production is extremely problematic, costly and time consuming.

The development of a packaging system that provides all the helper functions needed for rAAV production from a rAAV producer cell line would greatly facilitate the large-scale production of rAAV. Transfection procedures would not be required and the producer cell line could be grown in large quantities at high densities in commercially available laboratory equipment.

2.0 SUMMARY OF THE INVENTION

The present invention overcomes these and other inherent limitations in the prior art by providing packaging systems that provide all of the required helper functions, and methods for the large-scale production of rAAV. The present invention demonstrates the ability of a recombinant herpes simplex virus (rHSV) or a rHSV amplicon expressing AAV Rep and Cap to support replication and packaging of rAAV. The present methods overcome the need for transfection procedures, and provide reliable, cost-effective means for generating large quantities of rAAV. Superinfection of appropriate host cell cultures with the vectors described herein produces quantities of rAAV not attainable by any other means. By providing a second virus or cell line that contains the rAAV provirus, the present methods overcome the significant problem of spontaneous deletions in the AAV ITR when growing rAAV-based plasmids in bacterial cell cultures.

The present invention provides the first system that supplies AAV genes rep and cap and the HSV-1 helper functions needed for rAAV production in one delivery vehicle. The rHSV-1 and rHSV-1 amplicon-based vector systems supply Rep, Cap and the HSV-1 helper functions required for rAAV production. Amplicon and virus stocks have been produced that express Rep and Cap from their native promoters (p5, p19 and p40). To increase the yield of rAAV production and make the rHSV-1 and rHSV-1 amplicon systems practical alternatives to adenoviral systems for rAAV production, HSV-1 amplicon and vector systems that expresses Rep and Cap from their native promoters and uses an ICP27 mutated HSV-1 virus, d27-1, as the genetic background of the amplicon or vector has been developed. Use of the defective HSV-1 amplicon or vector results in rAAV production with an efficiency that exceeds previously described methods (Flotte et al., 1995). Southern blot and PCR™ analyses have shown that no wt AAV were produced using these modified amplicons or helper viruses. The present system provides means for increasing the scale of rAAV production to a level such that sufficient rAAV can now be produced for preclinical and clinical trials utilizing rAAV-based vectors for gene delivery.

The present invention provides DNA segments comprising an AAV rep coding sequence operably linked to a promoter, an AAV cap coding sequence operably linked to a promoter, an HSV-1 origin of replication and an HSV-1 packaging sequence. In preferred embodiments, the AAV rep coding sequence and/or the AAV cap coding sequence is operably linked to a p5, p19 or p40 promoter. In certain embodiments, the DNA segment is comprised within a recombinant herpes simplex virus vector, or within a recombinant herpes simplex virus capsid.

As used herein in this context, the term "recombinant herpes simplex virus vector" will be understood to mean genomic DNA of the herpes simplex virus with non-herpes simplex virus DNA added by the hand of man. The term "recombinant herpes simplex virus capsid", as used herein in this context will be understood to mean the herpes simplex virus head, comprised of herpes simplex virus capsid proteins, comprising a recombinant DNA segment, such as a plasmid, cosmid or the in like, that comprises at least an HSV-1 origin of replication and an HSV-1 packaging sequence.

Thus, the present invention also provides recombinant herpes simplex virus vectors comprising an AAV rep coding sequence operably linked to a promoter and an AAV cap coding sequence operably linked to a promoter. In preferred aspects of the invention, the AAV rep coding sequence and/or the AAV cap coding sequence is operably linked to a p5, p19 or p40 promoter.

In certain recombinant herpes simplex virus vectors of the present invention, a non-essential HSV gene is altered. In particular embodiments, the non-essential HSV gene is altered to increase expression. In a general sense, genes that encode proteins that are beneficial to the host cell, or that increase the production of rAAV particles are contemplated for such alteration. Examples of non-essential HSV genes that are altered to increase expression includes, but is not limited to, the HSV gene encoding ICP8.

In other embodiments, the non-essential HSV gene is mutated, such as by one or more point mutants or insertions, or substantially or completely deleted, such that the gene product of the non-essential HSV gene is either non-functional or absent. In a general sense, genes that encode proteins that are deleterious to the host cell, or that decrease the production of rAAV particles are contemplated for such alteration. Examples of non-essential HSV genes that are contemplated for mutation or deletion include, but are not limited to, the HSV genes encodes ICP27, an HSV late gene and/or glycoprotein H.

In preferred embodiments of the invention, the recombinant vector is comprised within a recombinant herpes simplex virus. As used herein in his context, the term "recombinant herpes simplex virus" will be understood to mean a complete herpes simplex virus that comprises a "recombinant herpes simplex virus vector", as defined above.

Therefore, the present invention further provides recombinant herpes simplex viruses comprising an AAV rep coding sequence operably linked to a promoter and an AAV cap coding sequence operably linked to a promoter. In preferred aspects of the invention, the AAV rep coding sequence and/or the AAV cap coding sequence is operably linked to a p5, p19 or p40 promoter.

In certain recombinant viruses of the present invention, a non-essential HSV gene is altered. In particular embodiments, the non-essential HSV gene is altered to increase expression. Examples of non-essential HSV genes that are altered to increase expression includes, but is not limited to, the HSV gene encoding ICP8. In other embodiments, the non-essential HSV gene is mutated, such as by one or more point mutants or insertions, or substantially or completely deleted, such that the gene product of the non-essential HSV gene is either non-functional or absent. Examples of non-essential HSV genes that are contemplated for mutation or deletion include, but are not limited to, the HSV genes encodes ICP27, an HSV late gene and/or glycoprotein H. In preferred embodiments, the recombinant virus is the d27.1rc virus.

The present invention also provides kits comprising, in a suitable container, a DNA segment comprising an AAV rep coding sequence operably linked to a promoter, an AAV cap coding sequence operably linked to a promoter, an HSV-1 origin of replication and an HSV-1 packaging sequence. In further aspects of the invention, the kit comprises an HSV-1 helper virus. In preferred aspects, a non-essential gene of the HSV-1 helper virus is altered. As detailed above, in certain aspects of the invention, a non-essential gene of the HSV-1 helper virus, exemplified by, but not limited to the gene encoding ICP8, is altered to increase expression. In other aspects, a non-essential gene of the HSV-1 helper virus, including, but not limited to the genes encoding ICP27 and/or glycoprotein H, is mutated or substantially deleted In certain preferred embodiments, the HSV-1 helper virus is the d27.1 HSV-1 virus.

Additionally, the present invention provides kits comprising, in a suitable container, a recombinant herpes simplex virus vector comprising an AAV rep coding sequence operably linked to a promoter and an AAV cap coding sequence operably linked to a promoter. In preferred kits of the invention, the recombinant herpes simplex virus vector is comprised in a recombinant herpes simplex virus.

The present invention also provides methods for preparing a rAAV comprising providing an HSV-1 helper virus and a DNA segment comprising an AAV rep coding sequence operably linked to a promoter, an AAV cap coding sequence operably linked to a promoter, an HSV-1 origin of replication and an HSV-1 packaging sequence to a host cell that comprises a rAAV, culturing the cell under conditions effective to produce rAAV in the cell, and obtaining the rAAV from the cell. As used herein in this context, the term "host cell that comprises a rAAV" will be understood to include a host cell that comprises a rAAV provirus integrated into the genome of the host cell, as well as a host cell that is infected with a rAAV. Thus, in certain aspects, the host cell comprises the rAAV integrated into the genome of the cell, while in other aspects the host cell is provided with the rAAV, the HSV-1 helper virus and the DNA segment simultaneously.

Preferred host cells include, but are not limited to, HeLa, 293 or Vero cells. In certain preferred methods of the invention, the rAAV comprises an AAV-2 genome. However, while the preferred rAAV genome is generally the AAV-2 genome, the capsid can be from any serotype of AAV. Therefore, in particular methods, the rAAV comprises an AAV-1, AAV-2, AAV-3, AAV-4, AAV-5 or AAV-6 capsid. As the present compositions and methods are designed for large-scale production of rAAV vectors, in preferred embodiments, the rAAV comprises a therapeutic gene. In certain methods, the AAV rep coding sequence and/or the AAV cap coding sequence is operably linked to a p5, p19 or p40 promoter. In other methods, at least a first AAV capsid protein is operably linked to an HSV late promoter, such as the HSV 110 promoter.

As detailed above, in certain methods of the present invention a non-essential gene of the HSV-1 helper virus is altered. In certain methods, a non-essential gene of the HSV-1 helper virus, exemplified by, but not limited to the gene encoding ICP8, is altered to increase expression. In other methods, a non-essential gene of the HSV-1 helper virus, including, but not limited to the genes encoding ICP27 and/or glycoprotein H, is mutated or substantially deleted. In certain preferred methods, the HSV-1 helper virus is the d27.1 HSV-1 virus. Thus, the present invention further provides a recombinant AAV virus produced by any of the methods of the present invention, as well as kits comprising, in a suitable container, a recombinant AAV virus produced by any of the methods of the present invention.

The present invention additionally provides methods for preparing a rAAV comprising providing a recombinant herpes simplex virus that comprises an AAV rep coding sequence operably linked to a promoter and an AAV cap coding sequence operably linked to a promoter to a host cell that comprises a rAAV, culturing the cell under conditions effective to produce rAAV in the cell, and obtaining the rAAV from the cell.

As detailed above, in certain methods a non essential gene of the recombinant herpes simplex virus, such as the gene encoding ICP8, is altered to increase expression, while in other methods, a non-essential gene of the recombinant herpes simplex virus, such as the gene encoding ICP27 or glycoprotein H, is mutated or substantially or completely deleted.

3.0 BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 1 shows a map of pHSV-RC, which was used to generate amplicons that replicate and package rAAV virions. The plasmid is a pUC-based vector. The a-sequence contains the HSV-1 packaging signals and is cloned into the EcoRI site. The 110-sequence contains an HSV-1 origin of replication and is the internal SmaI fragment from the HSV-1 ori S. The 110-sequence is inserted in the SmaI site. (The 110 and a-sequence containing plasmid is p110a) Rep and cap are the AAV-2 rep and cap genes isolated from psub201 by an XbaI digest and cloned into the XbaI site of p110a to create pHSV-RC.

Figure 2:
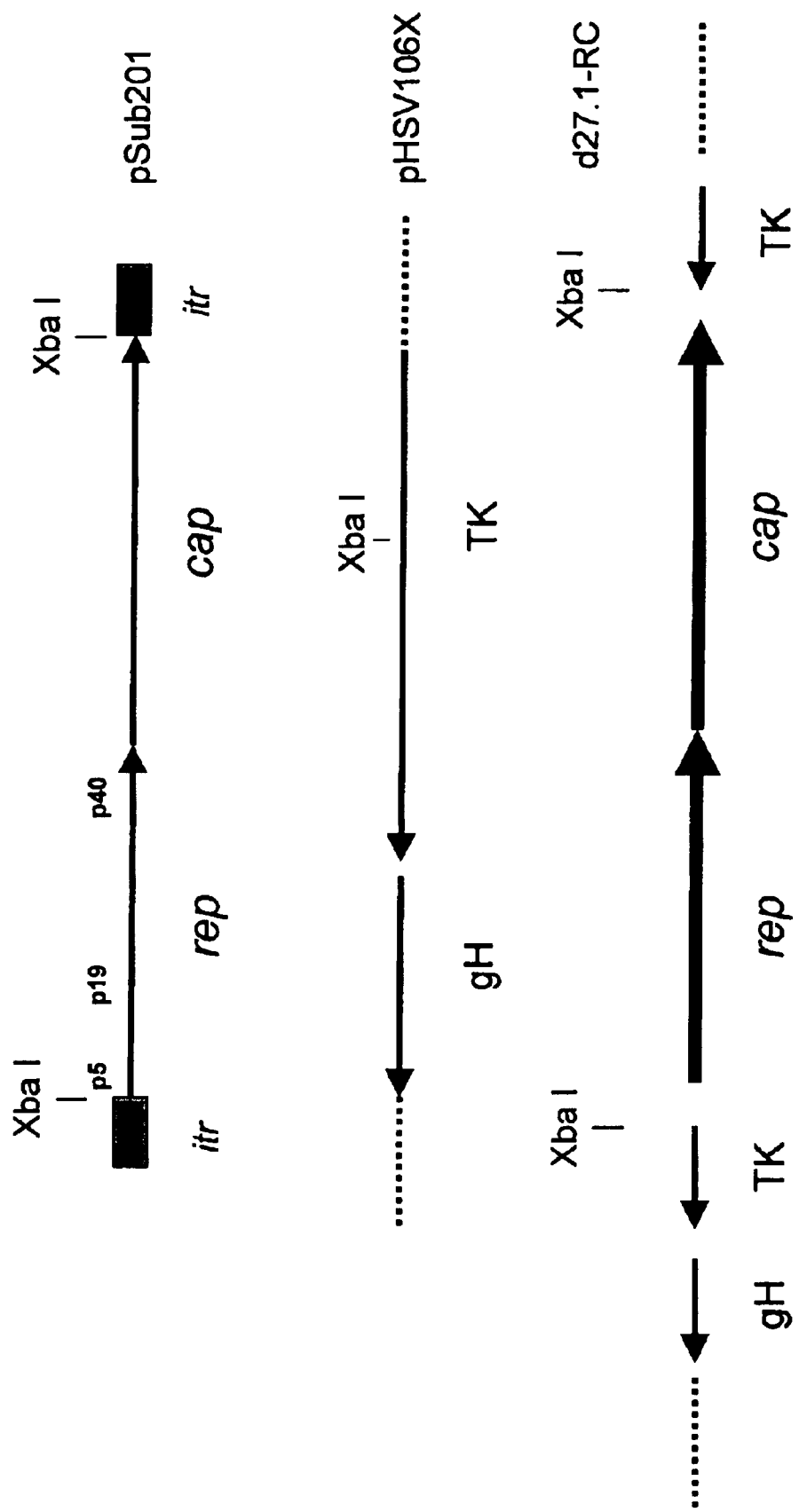

FIG. 2 shows the integration vector used to produce d27.1-rc. The plasmid pHSV-106 contains the BamHI fragment encoding the tk gene of HSV-1. The AAV-2 rep and cap genes, under control of their native promoters, were cloned into the KpnI site of tk gene to generate pHSV-106-rc. Restriction digest of pHSV-106-rc with SphI was used to generate the linear fragment. This fragment was cotransfected with d27.1-lacZ infected cell DNA into V27 cells to generate d27.1-rc by homologous recombination.

Figure 3:
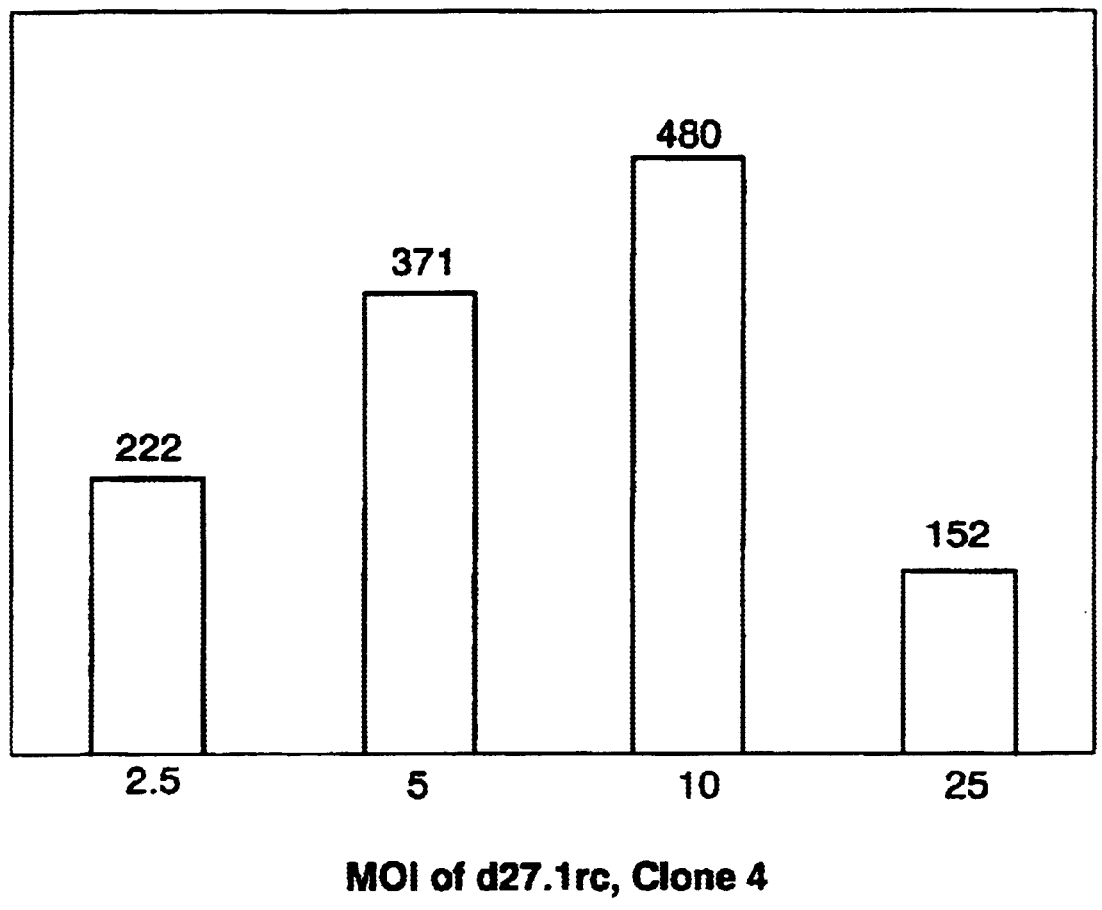

FIG. 3 demonstrates that recombinant adeno-associated virus can be amplified after coinfection with d27.1-rc. 293 cells were transfected with AAV-GFP proviral plasmid. Approximately $3 \times 10^7$ cells were present in each group. 24 h after transfection, the cells were superinfected with different MOIs of d27.1-rc. 36 h post infection, a cell lysate was made from the infected cells by three rounds of freeze-thaw. The viral lysate was heat inactivated at 55° C. for one hour and then titered in duplicate on C12 cells that were coinfected with Ad (MOI of 20). 48 h post infection the C12 cells were analyzed for GFP expression using fluorescent microscopy and a titer was determined (in expression units). The amount of AAV-GFP produced per transfected cell was then calculated. This study was repeated three times.

Figure 4:
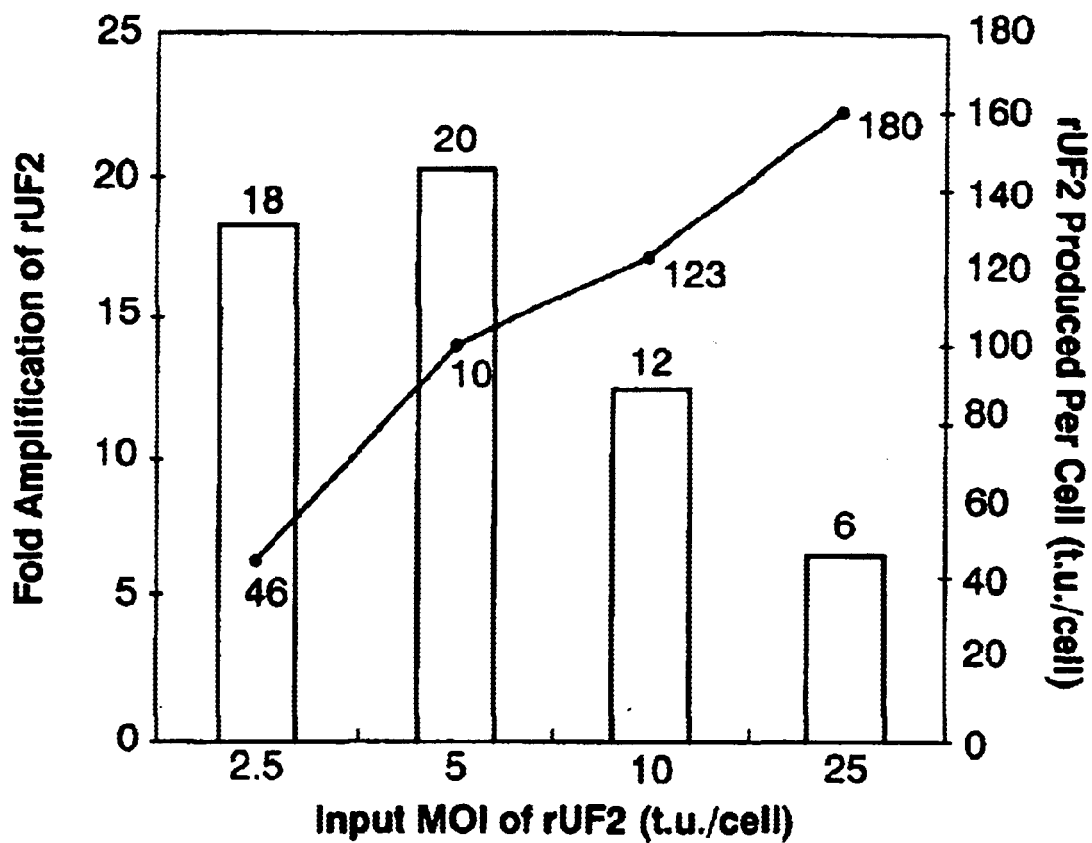

FIG. 4 illustrates that the vector d27.1-rc can produce rAAV from a proviral cell line. The cell line GFP-92 is a 293 derived cell line that has a single copy of AAV-GFP integrated into its genome. The vector d27.1-rc was used to produce AAV-GFP from this cell line. $1.5 \times 10^7$ GFP-92 cells were infected with d27.1-rc at different MOIs. 48 h post-infection a cell lysate was made from the infected cells by three rounds of freeze-thaw. The viral lysate was heat inactivated at 55° C. for one hour and then titered in duplicate on C12 cells that were coinfected with Ad (MOI of 20). 48 h post-infection the C12 cells were analyzed for GFP expression using fluorescent microscopy and a titer was determined (expression units). The amount of AAV-GFP produced per transfected cell was then calculated. This study was repeated three times.

4.0 DESCRIPTION OF ILLUSTRATIVE EMBODIMENTS

4.1 Construction of Modified Gene Therapy Vectors

Amplicons and viral vectors have been constructed that contain the AAV rep and cap genes under control of their native promoters (p5, p19 and p40). HSV-1 amplicons and viral vectors (HSV-RC/KOS, HSV-RC/d27 and HSV-AAV-GFP) were generated by supplying helper functions with either wild type HSV-1 (KOS strain) or the ICP27 immediate early mutant of HSV-1, d27-1, respectively, by homologous recombination using the targeting vector shown in FIG. 2. Growth of the amplicon or recombinant virus stock is not inhibited in the presence of Rep protein, which highlights important differences between HSV-1 and adenovirus (Ad) replication and the mechanism of providing helper function for productive AAV infection. Co-infection of rAAV and HSV-RC/d27 (also termed d27.1rc) results in the replication and amplification of rAAV genomes.

Similarly, rescue and replication of rAAV genomes are possible when recombinant vector plasmids were transfected into cells followed by d27.1rc infection. Production of infectious rAAV by rescue from two rAAV producer cell lines has also been achieved using both HSV-RC/KOS and HSV-RC/d27. The titer of rAAV produced using HSV-RC/d27 is similar to that achieved by supplying rep and cap by the most efficient transfection method developed utilizing adenovirus. Importantly, no detectable wild type AAV is generated using this approach. These results demonstrate that rHSV amplicons and vectors expressing the AAV rep and cap genes support the replication and packaging of rAAV vectors in a scaleable process, allowing for large-scale production of vector.

The HSV-RC/KOS and HSV-RC/d27 amplicons were able to replicate and amplify all forms of proviral rAAV. These amplicons are useful in replication center assays and also for the detection of episomal or integrated proviral rAAV in cells previously infected with rAAV. While the amplicon demonstrates the ability of rHSV to replicate in the presence of rAAV, there is an advantage to having a single recombinant molecule that expresses rep and cap. Therefore, the rHSV, d27.1-rc was generated as described below.

The use of HSV-RC/KOS or HSV-RC/d27 eliminates the need for coinfection of cells with wild-type (wt) AAV and adenovirus, and helps standardize problematic assays, which are difficult to reproduce. Eliminating the use of wt AAV is also desirable since it reduces the likelihood of wt AAV contamination of viral preparations and cells.

A producer cell line was able to produce rAAV vector when infected with HSV-RC/KOS. However, although HSV-RC/KOS could express all of the helper functions needed for rAAV production, this system was extremely inefficient A defective HSV-1 vector, d27-1, which overexpresses the HSV-1 helper genes required for AAV replication, was then used to make the second Rep and Cap expressing amplicon, HSV-RC/d27. The HSV-RC/d27 alone was shown to be capable of providing all of the helper functions required for rAAV replication and packaging. Infection with HSV-RC/d27 was capable of producing rAAV particles as efficiently as transfection methods. Infection with HSV-RC/d27 followed by HSV-1 superinfection was able to produce rAAV particles more efficiently than transfection methods. The rAAV virus produced by the HSV-1 amplicons was infectious after heat inactivation and CsCl gradient purification. Finally, wt AAV was not detected in any of the HSV-1 amplicon produced rAAV preparations.

4.2 Large-Scale Production of Modified Gene Therapy Vectors

Purification of rAAV intended for clinical trials will be facilitated by the disclosed amplicons and viral vectors. HSV-1 is a large enveloped virus greater than 200 nm in diameter (Roizman and Sears, 1996). The HSV-1 virion is extremely sensitive to heat and chemical inactivation. Additionally, size exclusion chromatography is extremely effective at eliminating HSV-1 virions from the rAAV preparations. This is likely due to the large size difference between the AAV capsid (20 nm diameter) and HSV-1 virion. Chromatographic methods have been developed to increase the efficiency of rAAV production by eliminating the need for CsCl gradients (Tamayose et al., 1997). Size exclusion chromatography may be easily be added to these production processes.

The present invention allows for the large-scale growth of host cells that contain infectious rAAV particles. In general, approximately $10^{11}$ to $10^{12}$ cells, each containing approximately 500 infectious particles per cell, are needed for the production of sufficient rAAV particles for use in gene therapy of patients. Previously, the growth of this number of cells would have taken approximately one year. Using the methods disclosed herein, the time need to grow this number of host cells can be reduced to as little as two weeks or so. Large scale growth of host cells for rAAV production can be facilitated using the methods disclosed herein, and modern apparatus for cell growth, such as that disclosed in U.S. Pat. No. 5,501,971, incorporated herein by reference in its entirety.

Substitution of heterologous promoters such as the HIV LTR or the HCMV IE promoter to drive Rep or Cap expression has been shown to increase the production of rAAV in transfection systems (Flotte et al., 1995; Vincent et al., 1997a). Constructs where Rep and Cap are expressed from these promoters are easily incorporated into the amplicon plasmid. Alternatively, one may use HSV-1 viral promoters incorporating VP16 responsive elements such as the HSV-1 IE-110 promoter to drive cap expression. The transactivating properties of the HSV-1 virion factor VP-16 would increase Cap expression, and increase rAAV production. Amplification of rAAV virions from a cell lysate using an HSV-1 amplicon system is also contemplated, eliminating the need for proviral cell lines and large-scale transfections. Stepwise coinfections may then be utilized to amplify the quantity of rAAV vector as is commonly done for other recombinant viruses that replicate in complementing cell lines.

Clearly, Rep does not disrupt HSV-1 replication as completely as it does adenovirus replication. One member of the herpes virus family, HHV-6, actually encodes and expresses a functional Rep homologue (Thomson and Efstathiou, 1991; Thomson et al., 1994). In contrast, Rep potently disrupts the replication of adenovirus and has made the production of p5 driven rep recombinant Ad unsuccessful to date. The creation of inducible promoter driven rep recombinant adenoviruses has also been problematic. While Rep has been shown to decrease HSV-1 viral DNA replication, it clearly does not preclude construction of amplicons, which express a functional Rep.

AAV-2 infection results in the AAV-2 genome entering a non-productive, non-progeny producing latent state where the viral genome exists as a provirus integrated into the host cell's chromosomal DNA (Cheung et al., 1980). Preferential integration of the wt AAV genome seems to occur via site specific, nonhomologous recombination in human cells at chromosome 19q13.3 (Kotin and Berns, 1989; Kotin et al., 1992; Kotin et al., 1990; Samulski et al., 1991). A productive lytic cycle ensues in which AAV DNA is replicated, amplified and packaged into progeny virions only during coinfection of AAV with the appropriate helper virus (adenovirus or herpes viruses) or infection of a latently infected cell with helper virus (Berns et al., 1988; Russell et al., 1995). Infection of wt AAV in the presence of DNA damaging agents also promotes viral replication through the induction of cellular DNA repair pathways.

The AAV DNA sequences, AAV viral proteins and helper virus genes that are required for productive wt AAV infection have been identified and have been utilized to produce rAAV vectors (Berns, 1984; Carter, 1990; Huang and Hearing, 1989; Mishra and Rose, 1990; Samulski and Shenk, 1988; Weindler and Heilbronn, 1991). The DNA sequences required for AAV replication that serve as origins of replication of the AAV genome and primers of second strand synthesis are located in the inverted terminal repeats (ITRs) of the AAV genome (Samulski et al., 1983). These sequences must be located cis to the recombinant genome that is to be replicated and packaged, and this rAAV genome is usually introduced into cells by transfection. The AAV Rep 78 or Rep 68 proteins, which direct replication of the genome from the ITRs, the viral Rep 52 and 40, which are necessary for efficient packaging, and the structural capsid proteins VP1, VP2 and VP3, are supplied in trans in the traditional packaging scheme, usually by transfection of Rep and Cap expressing plasmids (Samulski et al., 1987). Viral helper functions for AAV replication are usually supplied by adenoviral early gene expression of E1a, E1b, E2a, E4 and by VA RNA after adenovirus infection (Berns, 1984; Carter, 1990; Huang and Hearing, 1989; Samulski and Shenk, 1988).

Adenovirus has been the most thoroughly studied AAV helper virus, and the virus generally utilized to produce rAAV. The adenovirus helper functions required for AAV-2 or rAAV replication are probably not involved in AAV DNA synthesis directly. Instead, the adenoviral helper genes make AAV replication possible through regulation of cellular gene expression and regulation of rep expression (Im and Muzyczka, 1990). Attempts to use Ad vectors to carry AAV genes have met with failure, presumably because the AAV rep gene is not tolerated by Ad.

Like adenovirus, HSV-1 is a fully competent helper virus for wt AAV replication and packaging (Johnston et al., 1997; Mishra and Rose, 1990; Weindler and Heilbronn, 1991). In contrast to adenovirus, however, the helper functions provided by HSV-1 are due to the activities of replication proteins and not transcriptional regulators (Weindler and Heilbronn, 1991). The minimal set of HSV-1 genes required for efficient AAV replication and encapsidation include UL5, UL8, UL52 and UL29 (Weindler and Heilbronn, 1991). The genes UL5, UL8, and UL52 encode components of the HSV-1 helicase-primase complex (Crute et al., 1989). UL29 encodes a single-stranded DNA binding protein (Knipe et al., 1982). These four proteins essential for AAV DNA replication are components of the HSV-1 core replication machinery along with the HSV-1 DNA polymerase (UL30), the polymerase-accessory factor (UL42) and the origin binding protein (UL9) (Challberg, 1986; Wu et al., 1988). The genes UL5, UL8, UL52, and UL29 are transcribed early in infection preceding HSV-1 DNA replication and are absolutely required for HSV-1 DNA replication (Roizman and Sears, 1996). AAV replication and packaging can occur in the absence of HSV-1 DNA replication as long as HSV-1 early gene expression occurs (Weindler and Heilbronn, 1991).

4.3 Incorporation of rAAV Vectors into Cells

In various embodiments of the invention, DNA is delivered to a cell as an expression construct Preferred gene therapy vectors of the present invention are generally viral vectors.

Adeno-associated virus (AAV) is particularly attractive for gene transfer because it does not induce any pathogenic response and can integrate into the host cellular chromosome (Kotin et al., 1990). The AAV terminal repeats (TRs) are the only essential cis-components for the chromosomal integration (Muzyczka and McLaughlin, 1988). These TRs are reported to have promoter activity (Flotte et al., 1993). They may promote efficient gene transfer from the cytoplasm to the nucleus or increase the stability of plasmid DNA and enable longer-lasting gene expression. Studies using recombinant plasmid DNAs containing AAV TRs have attracted considerable interest AAV-based plasmids have been shown to drive higher and longer transgene expression than the identical plasmids lacking the TRs of AAV in most cell types (Shafron et al., 1998).

AAV (Ridgeway, 1988; Hermonat and Muzyczka, 1984) is a parovirus, discovered as a contamination of adenoviral stocks. It is a ubiquitous virus (antibodies are present in 85% of the US human population) that has not been linked to any disease. It is also classified as a dependovirus, because its replication is dependent on the presence of a helper virus, such as adenovirus. Five serotypes have been isolated, of which AAV-2 is the best characterized. AAV has a single-stranded linear DNA that is encapsidated into capsid proteins VP1, VP2 and VP3 to form an icosahedral virion of 20 to 24 nm in diameter (Muzyczka and McLaughlin, 1988).

The AAV DNA is approximately 4.7 kilobases long. It contains two open reading frames and is flanked by two ITRs. There are two major genes in the AAV genome: rep and cap. The rep gene encodes a protein responsible for viral replication, whereas cap encodes the capsid protein, VP1–3. Each ITR forms a T-shaped hairpin structure. These terminal repeats are the only essential cis components of the AAV for chromosomal integration. Therefore, the AAV can be used as a vector with all viral coding sequences removed and replaced by the cassette of genes for delivery. Three viral promoters have been identified and named p5, p19, and p40, according to their map position. Transcription from p5 and p19 results in production of Rep proteins, and transcription from p40 produces the Cap proteins (Hermonat and Muzyczka, 1984).

There are several factors that prompted researchers to study the possibility of using rAAV as an expression vector. One is that the requirements for delivering a gene to integrate into the host chromosome are surprisingly few. It is necessary to have the 145-bp ITRs, which are only 6% of the AAV genome. This leaves room in the vector to assemble a 4.5-kb DNA insertion. AAV is also a good choice of delivery vehicles due to its safety. There is a relatively complicated rescue mechanism: not only wild type adenovirus but also AAV genes are required to mobilize rAAV. Likewise, AAV is not pathogenic and not associated with any disease. The removal of viral coding sequences minimizes immune reactions to viral gene expression, and therefore, rAAV does not evoke an inflammatory response. AAV therefore, represents an ideal candidate for delivery of the present hammerhead ribozyme constructs.

Retroviruses have promise as gene delivery vectors due to their ability to integrate their genes into the host genome, transferring a large amount of foreign genetic material, infecting a broad spectrum of species and cell types and of being packaged in special cell-lines.

Of course, in using viral delivery systems, one will desire to purify the virion sufficiently to render it essentially free of undesirable contaminants, such as defective interfering viral particles or endotoxins and other pyrogens such that it will not cause any untoward reactions in the cell, animal or individual receiving the vector construct. A preferred means of purifying the vector involves the use of buoyant density gradients, such as cesium chloride gradient centrifugation, heparin affinity chromatography (Clark et al., 1999), or non-ionic iodixinol gradients followed by heparin affinity chromatography (Zolotukhin et al., 1999).

The titer of AAV in a given sample may be determined using any one of the methods routinely accepted in the AAV arts. For example, the inventors routinely use the methods of QC-PCR™ or infectious center assay, as described in detail in the Examples and by Zolotukhin et al. (1999), to determine the titer of a viral stock.

Likewise, the infectivity of a given AAV sample may be determined using any one of the methods routinely accepted in the AAV arts. For example, the inventors routinely use the methods of Hermonat and Muzyczka (1984) or Clark et al. (1999) to determine the infectivity of a given AAV stock.

The titer and infectivity of HSV in a given sample may also be determined using any one of the conventional methods known to those of skill in the art. For example, the methods described in detail in Example 9, below, are routinely employed by the inventors to determine the titer and infectivity of an HSV viral stock. Infectivity and titer are equivalent for HSV, since plaque-forming units are measured.

4.4 Herpes Simplex Virus

As described in U.S. Pat. No. 5,879,934 (specifically incorporated herein by reference in its entirety), Herpes simplex virus (HSV) comprises a double-stranded, linear DNA genome that encodes approximately 80 genes and consists of an approximately 152-kb nucleotide sequence. The viral genes are transcribed by cellular RNA polymerase II and are temporally regulated, resulting in the transcription and subsequent synthesis of gene products in roughly three discernable phases. These phases are referred to as the Immediate Early (IE, or $\alpha$), Early (E, or $\beta$) and Late (L, or $\gamma$) genes. Immediately following the arrival of the genome of a virus in the nucleus of a newly infected cell, the IE genes are transcribed. The efficient expression of these genes does not require prior viral protein synthesis. The products of IE genes are required to activate transcription and regulate the remainder of the viral genome.

One IE protein, Infected Cell Polypeptide 4 (ICP4), also known as $\alpha$4, or Vmw175, is absolutely required for both virus infectivity and the transition from IE to later transcription (DeLuca et al., 1987; DeLuca et al., 1988; Paterson et al., 1988a; 1988b; Shepard et al., 1989; Shepard et al., 1991).

U.S. Pat. No. 5,879,934 teaches that several reports have described the use of viruses deleted in ICP4 for gene transfer (Breakefield et al., 1991; Chocca et al., 1990). One property of viruses deleted for ICP4 that makes them desirable for gene transfer is that they only express the five other IE genes: ICP0, IC6, ICP27, ICP22 and ICP47 (DeLuca et al., 1985). This excludes the expression of viral genes encoding proteins that direct viral DNA synthesis, as well as the structural proteins of the virus, which is desirable because it minimizes possible deleterious effects on host cell metabolism following gene transfer.

4.5 Methods of Nucleic Acid Delivery and DNA Transfection

In some embodiments, it may be desirable to use other methods for the transfer of expression constructs into target mammalian cells. Some of these techniques may be successfully adapted for in vivo or ex vivo use, as discussed below. Likewise, in some applications, it may be desirable to transfer a naked DNA expression construct into cells using methods such as particle bombardment. This method depends on the ability to accelerate DNA coated microprojectiles to a high velocity allowing them to pierce cell membranes and enter cells without killing them. Several devices for accelerating small particles have been developed. One such device relies on a high voltage discharge to generate an electrical current, which in turn provides the motive force. The microprojectiles used have consisted of biologically inert substances such as tungsten or gold beads.

In certain embodiments, it is contemplated that one or more polynucleotide compositions disclosed herein will be used to transfect an appropriate host cell. Technology for introduction of nucleic acids into cells is well known to those of skill in the art. These include calcium phosphate precipitation (Graham and Van Der Eb, 1973; Chen and Okayama, 1987; Rippe et al., 1990) DEAE-dextran (Gopal, 1985), electroporation (Wong and Neumann, 1982; Fromm et al., 1985; Tur-Kaspa et al., 1986; Potter et al., 1984; Suzuki et al., 1998; Vanbever, et al., 1998), direct microinjection (Capecchi, 1980; Harland and Weintraub, 1985), DNA-loaded liposomes (Nicolau and Sene, 1982; Fraley et al., 1979; Takakura, 1998) and lipofectamine-DNA complexes (Fechheimer et al., 1987), gene bombardment using high velocity microprojectiles (Yang et al., 1990; Klein et al., 1992), and receptor-mediated transfection (Curiel et al., 1991; Wagner et al., 1992; Wu and Wu, 1987; Wu and Wu, 1988). Some of these techniques may be successfully adapted for in vivo or ex vivo use.

4.6 Liposome and Nanocapsule Formulations

In a further embodiment of the invention, the rAAV vectors and related expression constructs may be formulated by entraping within a liposome, nanocapsule, microcapsule, lipofectamine-DNA complex, or other suitable lipid particle, as discussed below. In certain embodiments, the inventors contemplate the use of liposomes, nanocapsules, microparticles, microspheres, lipid particles, vesicles, and the like, for the introduction of the viral compositions of the present invention into suitable host cells.

Liposome-mediated nucleic acid delivery and expression of foreign DNA in vitro has been very successful. Wong et al. (1980) demonstrated the feasibility of liposome-mediated delivery and expression of foreign DNA in cultured chick embryo, HeLa and hepatoma cells. In certain embodiments of the invention, the liposome may be complexed with a hemagglutinating virus (HVJ). This has been shown to facilitate fusion with the cell membrane and promote cell entry of liposome-encapsulated DNA. In other embodiments, the liposome may be complexed or employed in conjunction with nuclear non-histone chromosomal proteins (HMG-1). In yet further embodiments, the liposome may be complexed or employed in conjunction with both HVJ and HMG-1. In other embodiments, the delivery vehicle may comprise a ligand and a liposome.

Such formulations may be preferred for the introduction of pharmaceutically acceptable formulations of the viral vectors disclosed herein. The formation and use of liposomes is generally known to those of skill in the art (see for example, Couvreur et al., 1977; Couvreur, 1988; Lasic, 1998; which describes the use of liposomes and nanocapsules in the targeted antibiotic therapy for intracellular bacterial infections and diseases). Recently, liposomes were developed with improved serum stability and circulation half-lives (Gabizon and Papahadjopoulos, 1988; Allen and Choun, 1987; U.S. Pat. No. 5,741,516, specifically incorporated herein by reference in its entirety). Further, various methods of liposome and liposome like preparations as potential drug carriers have been reviewed (Takakura, 1998; Chandran et al., 1997; Margalit, 1995; U.S. Pat. Nos. 5,567,434; 5,552,157; 5,565,213; 5,738,868 and 5,795,587, each specifically incorporated herein by reference in its entirety).

Liposomes have been used successfully with a number of cell types that are normally resistant to transfection by other procedures including T cell suspensions, primary hepatocyte cultures and PC 12 cells (Renneisen et al., 1990; Muller et al., 1990). In addition, liposomes are free of the DNA length constraints that are typical of viral-based delivery systems. Liposomes have been used effectively to introduce genes, drugs (Heath and Martin, 1986; Heath et al., 1986; Balazsovits et al., 1989; Fresta and Puglisi, 1996), radiotherapeutic agents (Pikul et al., 1987), enzymes (Imaizumi et al., 1990a; Imaizumi et al., 1990b), viruses (Faller and Baltimore, 1984), transcription factors and allosteric effectors (Nicolau and Gersonde, 1979) into a variety of cultured cell lines and animals. In addition, several successful clinical trails examining the effectiveness of liposome-mediated drug delivery have been completed (Lopez-Berestein et al., 1985a; 1985b; Coune, 1988; Sculier et al., 1988). Furthermore, several studies suggest that the use of liposomes is not associated with autoimmune responses, toxicity or gonadal localization after systemic delivery (Mori and Fukatsu, 1992).

Liposomes are formed from phospholipids that are dispersed in an aqueous medium and spontaneously form multilamellar concentric bilayer vesicles (also termed multilamellar vesicles (MLVs). MLVs generally have diameters of from 25 nm to 4 µm. Sonication of MLVs results in the formation of small unilamellar vesicles (SUVs) with diameters in the range of 200 to 500 Å, containing an aqueous solution in the core.

Liposomes bear resemblance to cellular membranes and are contemplated for use in connection with the present invention as carriers for the peptide compositions. They are widely suitable as both water- and lipid-soluble substances can be entrapped, i.e. in the aqueous spaces and within the bilayer itself, respectively. It is possible that the drug-bearing liposomes may even be employed for site-specific delivery of active agents by selectively modifying the liposomal formulation.

In addition to the teachings of Couvreur et al. (1977; 1988), the following information may be utilized in generating liposomal formulations. Phospholipids can form a variety of structures other than liposomes when dispersed in water, depending on the molar ratio of lipid to water. At low ratios the liposome is the preferred structure. The physical characteristics of liposomes depend on pH, ionic strength and the presence of divalent cations. Liposomes can show low permeability to ionic and polar substances, but at elevated temperatures undergo a phase transition which markedly alters their permeability. The phase transition involves a change from a closely packed, ordered structure, known as the gel state, to a loosely packed, less-ordered structure, known as the fluid state. This occurs at a characteristic phase-transition temperature, and results in an increase in permeability to ions, sugars, and drugs.

In addition to temperature, exposure to proteins can alter the permeability of liposomes. Certain soluble proteins such as cytochrome c bind, deform, and penetrate the bilayer, thereby causing changes in permeability. Cholesterol inhibits this penetration of proteins, apparently by packing the phospholipids more tightly. It is contemplated that the most useful liposome formations for antibiotic and inhibitor delivery will contain cholesterol.

The ability to trap solutes varies between different types of liposomes. For example, MLVs are moderately efficient at trapping solutes, but SUVs are extremely inefficient. SUVs offer the advantage of homogeneity and reproducibility in size distribution, however, and a compromise between size and trapping efficiency is offered by large unilamellar vesicles (LUVs). These are prepared by ether evaporation and are three to four times more efficient at solute entrapment than MLVs.

In addition to liposome characteristics, an important determinant in entrapping compounds is the physicocherical properties of the compound itself. Polar compounds are trapped in the aqueous spaces and nonpolar compounds bind to the lipid bilayer of the vesicle. Polar compounds are released through permeation or when the bilayer is broken, but nonpolar compounds remain affiliated with the bilayer unless it is disrupted by temperature or exposure to lipoproteins. Both types show maximum efflux rates at the phase transition temperature.

Liposomes interact with cells via four different mechanisms: Endocytosis by phagocytic cells of the reticuloendothelial system such as macrophages and neutrophils; adsorption to the cell surface, either by nonspecific weak hydrophobic or electrostatic forces, or by specific interactions with cell-surface components; fusion with the plasma cell membrane by insertion of the lipid bilayer of the liposome into the plasma membrane, with simultaneous release of liposomal contents into the cytoplasm; and by transfer of liposomal lipids to cellular or subcellular membranes, or vice versa, without any association of the liposome contents. It often is difficult to determine which mechanism is operative and more than one may operate at the same time.

The fate and disposition of intravenously injected liposomes depend on their physical properties, such as size, fluidity and surface charge. They may persist in tissues for h or days, depending on their composition, and half lives in the blood range from min to several h Larger liposomes, such as MLVs and LUVs, are taken up rapidly by phagocytic cells of the reticuloendothelial system, but physiology of the circulatory system restrains the exit of such large species at most sites. They can exit only in places where large openings or pores exist in the capillary endothelium, such as the sinusoids of the liver or spleen. Thus, these organs are the predominate site of uptake. On the other hand, SUVs show a broader tissue distribution but still are sequestered highly in the liver and spleen. In general, this in vivo behavior limits the potential targeting of liposomes to only those organs and tissues accessible to their large size. These include the blood, liver, spleen, bone marrow and lymphoid organs.

Targeting is generally not a limitation in terms of the present invention. However, should specific targeting be desired, methods are available for this to be accomplished. Antibodies may be used to bind to the liposome surface and to direct the antibody and its drug contents to specific antigenic receptors located on a particular cell-type surface. Carbohydrate determinants (glycoprotein or glycolipid cell-surface components that play a role in cell-cell recognition, interaction and adhesion) may also be used as recognition sites as they have potential in directing liposomes to particular cell types. Mostly, it is contemplated that intravenous injection of liposomal preparations would be used, but other routes of administration are also conceivable.

Alternatively, the invention provides for pharmaceutically acceptable nanocapsule formulations of the polynucleotide compositions of the present invention. Nanocapsules can generally entrap compounds in a stable and reproducible way (Henry-Michelland et al., 1987; Quintanar-Guerrero et al., 1998; Douglas et al., 1987). To avoid side effects due to intracellular polymeric overloading, such ultrafine particles (sized around 0.1 $\mu$m) should be designed using polymers able to be degraded in vivo. Biodegradable polyalkylcyanoacrylate nanoparticles that meet these requirements are contemplated for use in the present invention, and such particles may be are easily made, as described (Couvreur et al., 1980; 1988; zur Muhlen et al., 1998; Zambaux et al. 1998; Pinto-Alphandry et al., 1995 and U.S. Pat. No. 5,145,684, specifically incorporated herein by reference in its entirety

4.7 Pharmaceutical Compositions and Routes of Administration

In aspects of the invention involving administration of the vector compositions to an animal (e.g., in gene therapy of a human subject), the vector compositions are preferably dispersed in a pharmaceutically acceptable excipient or solution. The pharmaceutical compositions comprising the vector compositions may be administered parenterally, intraperitoneally or topically. Solutions of the active compounds as a free base or a pharmacologically acceptable salt may also be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with several of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

For ophthalmic delivery regimens, the vector compositions may also be advantageously administered extraocularly or intraocularly, by topical application, inserts, injection, implants, or by cell therapy or gene therapy. For example, slow-releasing implants containing the vector compositions embedded in a biodegradable polymer matrix can deliver the vector compositions intra ocularly. The vector compositions may also be administered extracerebrally in a form that has been modified chemically or packaged so that it passes the blood-brain barrier, or it may be administered in connection with one or more agents capable of promoting penetration of the vector compositions across the barrier. Similarly, the vector compositions may be administered intraocularly, or may be administered extraocularly in connection with one or more agents capable of promoting penetration or transport of the vector compositions across the membranes of the eye.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

The phrase "pharmaceutically acceptable" refers to molecular entities and compositions that do not produce an allergic or similar untoward reaction when administered to a human. The preparation of an aqueous composition that contains a protein as an active ingredient is well understood in the art. Typically, such compositions are prepared as injectables, either as liquid solutions or suspensions; solid forms suitable for solution in, or suspension in, liquid prior to injection can also be prepared. The preparation can also be emulsified.

The composition can be formulated in a neutral or salt form. Pharmaceutically acceptable salts, include the acid addition salts (formed with the free amino groups of the protein) and which are formed with inorganic acids such as, for example, hydrochloric or phosphoric acids, or such organic acids as acetic, oxalic, tatanc, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. Upon formulation, solutions will be administered in a manner compatible with the dosage formulation and in such amount as is therapeutically effective. The formulations are easily administered in a variety of dosage forms such as injectable solutions, drug release capsules and the like.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media that can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035–1038 and 1570–1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

4.8 Therapeutic Kits

Additional embodiments of the present invention concern therapeutic kits that comprise, in a suitable container means, at least a first, or at least a first and a second rAAV vector in a pharmaceutically acceptable formulation. The vector compositions may comprise one or more polynucleotide sequences that encode all, or portions of one or more genes targeted for delivery to a selected host cell by the rAAV vector. These genes may encode full-length proteins, truncated proteins, site-specifically mutated proteins, or peptide epitopes. In other embodiments, the rAAV vector may comprise nucleic acid segments that encode enhancers, transcription factors, structural or regulatory proteins, ribozymes, or fusion proteins, and the like. Such nucleic acid segments may be either native, recombinant, or mutagenized nucleic acid segments. Kits comprising at least a first rAAV construct and instructions for using the construct (e.g., in embodiments concerning gene therapy regimens) are also within the scope of the present invention. Such instructions may comprise information regarding the formulation, administration, dosage, or assay of the appropriate gene therapy constructs.

The kits may comprise a single container that may, if desired, contain a pharmaceutically acceptable sterile excipient, having associated with it the vector compositions. The single container means may contain a dry, or lyophilized, mixture of the viral vector composition, which may or may not require pre-wetting before use.

Alternatively, the kits of the invention may comprise a distinct container for each component. In such cases, separate or distinct containers would contain the viral vector, either as a sterile DNA solution or in a lyophilized form. The kits may also comprise a third container for containing a sterile, pharmaceutically acceptable buffer, diluent or solvent. Such a solution may be required to formulate the vector components into a more suitable form for application to the body, e.g., as an intravenous or other injectable form(s). It should be noted, however, that all components of a kit could be supplied in a dry form (lyophilized), which would allow for "wetting" upon contact with body fluids. Thus, the presence of any type of pharmaceutically acceptable buffer or solvent is not a requirement for the kits of the invention.

The container(s) will generally be a container such as a vial, test tube, flask, bottle, syringe or other container, into which the components of the kit may placed. The compositions may also be aliquoted into smaller containers, should this be desired. The kits of the present invention may also include material for containing the individual containers in close confinement for commercial sale, such as, e.g., injection or blow-molded plastic containers into which the desired vials or syringes are retained. Irrespective of the number of containers, the kits of the invention may also comprise, or be packaged with, an instrument for assisting with the placement of the vector compositions within the body of an animal. Such an instrument may be a syringe, pipette, forceps, or any such medically approved delivery vehicle. Likewise, the kit may also comprise one or more sets of instructions for use of the kit, for delivery of the vector to a selected host cell, or for storage and handling of the kit and its contents.

4.9 Kits for Large-scale Preparation of rAAV or HSV Vectors

Additional embodiments of the present invention concern kits that comprise, in a suitable container means, at least a first DNA segment comprising an AAV rep coding sequence operably linked to a promoter, an AAV cap coding sequence operably linked to a promoter, an HSV-1 origin of replication and an HSV-1 packaging sequence. Such kits may also comprise an HSV-1 helper virus.

The kits may comprise a single container that contains the DNA segment and the helper virus, or the DNA segment and helper virus may be contained in distinct containers. Kits that comprise a recombinant herpes simplex virus vector comprising an AAV rep coding sequence operably linked to a promoter and an AAV cap coding sequence operably linked to a promoter are also provided.

Such kits may also include material for containing the individual containers in close confinement for commercial sale, such as, e.g., injection or blow-molded plastic containers into which the desired vials or syringes are retained.

Irrespective of the number of containers, the kits of the invention may also comprise one or more sets of instructions for use of the kit, for delivery of the vector to a selected host cell, or for storage and handling of the kit and its contents. Such instructions may provide protocols for the large-scale preparation of the vector components, and may include such information as growth conditions, isolation and purification methodologies, and other parameters for preparation of the final vector compositions.

4.10 Nucleic Acid Amplification and Site-specific Mutagenesis

Site-specific mutagenesis is a technique useful in the preparation of individual peptides, or biologically functional equivalent polypeptides, through specific mutagenesis of the underlying polynucleotides that encode them. The technique, well-known to those of skill in the art, further provides a ready ability to prepare and test sequence variants, for example, incorporating one or more of the foregoing considerations, by introducing one or more nucleotide sequence changes into the DNA. Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Mutations may be employed in a selected polynucleotide sequence to improve, alter, decrease, modify, or change the properties of the polynucleotide itself, and/or alter the properties, activity, composition, stability, or primary sequence of the encoded polypeptide.

In certain embodiments of the present invention, the inventors contemplate the mutagenesis of the disclosed polynucleotide sequences to alter the activity or effectiveness of such viral vector constructs in a transformed host cell. Likewise in certain embodiments, the inventors contemplate the mutagenesis of the viral genome itself to facilitate improved infectivity, replication, stability, activity, or viral titers, as well as efficiency of transfection both in vitro and/or in vivo.

In general, site-directed mutagenesis in accordance herewith is performed by first obtaining a single-stranded vector or melting apart of two strands of a double-stranded vector which includes within its sequence a DNA sequence which encodes the desired polypeptide(s). An oligonucleotide primer bearing the desired mutated sequence is prepared, generally synthetically. This primer is then annealed with the single-stranded vector, and subjected to DNA polymerizing enzymes such as E. coli polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform appropriate cells, such as E. coli cells, and clones are selected which include recombinant vectors bearing the mutated sequence arrangement.

The preparation of sequence variants of the selected polynucleotide segments using site-directed mutagenesis is provided as a means of producing potentially useful species and is not meant to be limiting, as there are other ways in which sequence variants of polypeptides and the DNA sequences encoding them may be obtained. For example, recombinant vectors encoding a desired polypeptide sequence may be treated with mutagenic agents, such as hydroxylamnine, to obtain sequence variants. Specific details regarding these methods and protocols are found in the teachings of Maloy et al., 1994; Segal, 1976; Prokop and Bajpai, 1991; Kuby, 1994; and Maniatis et al., 1982, each incorporated herein by reference, for that purpose.

As used herein, the term "oligonucleotide directed mutagenesis procedure" refers to template-dependent processes and vector-mediated propagation that result in an increase in the concentration of a specific nucleic acid molecule relative to its initial concentration, or in an increase in the concentration of a detectable signal, such as amplification. As used herein, the term "oligonucleotide directed mutagenesis procedure" is intended to refer to a process that involves the template-dependent extension of a primer molecule. The term template dependent process refers to nucleic acid synthesis of an RNA or a DNA molecule wherein the sequence of the newly synthesized strand of nucleic acid is dictated by the well-known rules of complementary base pairing (see, for example, Watson, 1987). Typically, vector mediated methodologies involve the introduction of the nucleic acid fragment into a DNA or RNA vector, the clonal amplification of the vector, and the recovery of the amplified nucleic acid fragment. Examples of such methodologies are provided by U.S. Pat. No. 4,237,224, specifically incorporated herein by reference in its entirety. Nucleic acids, used as a template for amplification methods, may be isolated from cells according to standard methodologies (Sambrook et al., 1989). The nucleic acid may be genomic DNA or fractionated or whole cell RNA. Where RNA is used, it may be desired to convert the RNA to a complementary DNA. In one embodiment, the RNA is whole cell RNA and is used directly as the template for amplification.

Pairs of primers that selectively hybridize to nucleic acids corresponding to the ribozymes or conserved flanking regions are contacted with the isolated nucleic acid under conditions that permit selective hybridization. The term "primer," as defined herein, is meant to encompass any nucleic acid that is capable of priming the synthesis of a nascent nucleic acid in a template-dependent process. Typically, primers are oligonucleotides from ten to twenty base pairs in length, but longer sequences can be employed. Primers may be provided in double-stranded or single-stranded form, although the single-stranded form is preferred.

Once hybridized, the nucleic acid:primer complex is contacted with one or more enzymes that facilitate template-dependent nucleic acid synthesis. Multiple rounds of amplification, also referred to as "cycles," are conducted until a sufficient amount of amplification product is produced.

Next, the amplification product is detected. In certain applications, the detection may be performed by visual means. Alternatively, the detection may involve indirect identification of the product via chemiluminescence, radioactive scintigraphy of incorporated radiolabel or fluorescent label or even via a system using electrical or thermal impulse signals (Affymax technology).

A number of template dependent processes are available to amplify the marker sequences present in a given template sample. One of the best-known amplification methods is the polymerase chain reaction (referred to as PCR™) which is described in detail in U.S. Pat. Nos. 4,683,195, 4,683,202 and 4,800,159, and each incorporated herein by reference in entirety.

Briefly, in PCR™, two primer sequences are prepared that are complementary to regions on opposite complementary strands of the marker sequence. An excess of deoxynucleoside triphosphates is added to a reaction mixture along with a DNA polymerase, e.g., Taq polymerase. If the marker sequence is present in a sample, the primers will bind to the marker and the polymerase will cause the primers to be extended along the marker sequence by adding on nucleotides. By raising and lowering the temperature of the reaction mixture, the extended primers will dissociate from the marker to form reaction products, excess primers will bind to the marker and to the reaction products and the process is repeated.

A reverse transcriptase PCR amplification procedure may be performed in order to quantify the amount of mRNA amplified. Methods of reverse transcribing RNA into cDNA are well known and described in Sambrook et al., 1989. Alternative methods for reverse transcription utilize thermostable, RNA-dependent DNA polymerases. These methods are described in WO 90/07641, filed Dec. 21, 1990, incorporated herein by reference. Polymerase chain reaction methodologies are well known in the art.

Another method for amplification is the ligase chain reaction ("LCR"), disclosed in Eur. Pat. Appl. No. 320308, incorporated herein by reference in its entirety. In LCR, two complementary probe pairs are prepared, and in the presence of the target sequence, each pair will bind to opposite complementary strands of the target such that they abut. In the presence of a ligase, the two probe pairs will link to form a single unit. By temperature cycling, as in PCR, bound ligated units dissociate from the target and then serve as "target sequences" for ligation of excess probe pairs. U.S. Pat. No. 4,883,750 describes a method similar to LCR for binding probe pairs to a target sequence.

Qbeta Replicase (QβR), described in Intl. Pat. Appl. Publ. No. PCT/US87/00880, incorporated herein by reference, may also be used as still another amplification method in the present invention. In this method, a replicative sequence of RNA that has a region complementary to that of a target is added to a sample in the presence of an RNA polymerase. The polymerase will copy the replicative sequence that can then be detected.

An isothermal amplification method, in which restriction endonucleases and ligases are used to achieve the amplification of target molecules that contain nucleotide 5'-[alpha-thio]-triphosplites in one strand of a restriction site may also be useful in the amplification of nucleic acids in the present invention.

Strand Displacement Amplification (SDA), described in U.S. Pat. Nos. 5,455,166, 5,648,211, 5,712,124 and 5,744,311, each incorporated herein by reference, is another method of carrying out isothermal amplification of nucleic acids which involves multiple rounds of strand displacement and synthesis, i.e., nick translation. A similar method, called Repair Chain Reaction (RCR), involves annealing several probes throughout a region targeted for amplification, followed by a repair reaction in which only two of the four bases are present. The other two bases can be added as biotinylated derivatives for easy detection. A similar approach is used in SDA. Target specific sequences can also be detected using a cyclic probe reaction (CPR). In CPR, a probe having 3' and 5' sequences of non-specific DNA and a middle sequence of specific RNA is hybridized to DNA that is present in a sample. Upon hybridization, the reaction is treated with RNase H, and the products of the probe identified as distinctive products that are released after digestion. The original template is annealed to another cycling probe and the reaction is repeated.

Still another amplification methods described in Great Britain Pat. No. 2202328, and in Intl. Pat. Appl. Publ. No. PCT/US89/01025, each of which is incorporated herein by reference in its entirety, may be used in accordance with the present invention. In the former application, "modified" primers are used in a PCR-like, template- and enzyme-dependent synthesis. The primers may be modified by labeling with a capture moiety (e.g., biotin) and/or a detector moiety (e.g., enzyme). In the latter application, an excess of labeled probes is added to a sample. In the presence of the target sequence, the probe binds and is cleaved catalytically. After cleavage, the target sequence is released intact, available to be bound by excess probe. Cleavage of the labeled probe signals the presence of the target sequence.

Other nucleic acid amplification procedures include transcription-based amplification systems (TAS), including nucleic acid sequence based amplification (NASBA) and 3SR Gingeras et al., PCT Application WO 88/10315, incorporated herein by reference. In NASBA, the nucleic acids can be prepared for amplification by standard phenol/chloroform extraction, heat denaturation of a clinical sample, treatment with lysis buffer and minispin columns for isolation of DNA and RNA or guanidinium chloride extraction of RNA. These amplification techniques involve annealing a primer that has target specific sequences. Following polymerization, DNA/RNA hybrids are digested with RNase H while double stranded DNA molecules are heat denatured again. In either case the single stranded DNA is made fully double stranded by addition of second target specific primer, followed by polymerization. The double-stranded DNA molecules are then multiply transcribed by an RNA polymerase such as T7 or SP6. In an isothermal cyclic reaction, the RNA's are reverse transcribed into single stranded DNA, which is then converted to double-stranded DNA, and then transcribed once again with an RNA polymerase such as T7 or SP6. The resulting products, whether truncated or complete, indicate target specific sequences.

Davey et al., Eur. Pat. Appl. No. 329822 (incorporated herein by reference in its entirety) disclose a nucleic acid amplification process involving cyclically synthesizing single-stranded RNA ("ssRNA"), ssDNA, and double-stranded DNA (dsDNA), which may be used in accordance with the present invention. The ssRNA is a template for a first primer oligonucleotide, which is elongated by reverse transcriptase (RNA-dependent DNA polymerase). The RNA is then removed from the resulting DNA:RNA duplex by the action of ribonuclease H (RNase H, an RNase specific for RNA in duplex with either DNA or RNA). The resultant ssDNA is a template for a second primer, which also includes the sequences of an RNA polymerase promoter (exemplified by T7 RNA polymerase) 5' to its homology to the template. This primer is then extended by DNA polymerase (exemplified by the large "Klenow" fragment of E. coli DNA polymerase I), resulting in a double-stranded DNA ("dsDNA") molecule, having a sequence identical to that of the original RNA between the primers and having additionally, at one end, a promoter sequence. This promoter sequence can be used by the appropriate RNA polymerase to make many RNA copies of the DNA. These copies can then re-enter the cycle leading to very swift amplification. With proper choice of enzymes, this amplification can be done isothermally without addition of enzymes at each cycle. Because of the cyclical nature of this process, the starting sequence can be chosen to be in the form of either DNA or RNA.

Miller et al., PCT Application WO 89/06700 (incorporated herein by reference in its entirety) disclose a nucleic acid sequence amplification scheme based on the hybridization of a promoter/primer sequence to a target single-stranded DNA ("ssDNA") followed by transcription of many RNA copies of the sequence. This scheme is not cyclic, i.e., new templates are not produced from the resultant RNA transcripts. Other amplification methods include "RACE" and "one-sided PCR" (Frohman, 1990 incorporated by reference).

Methods based on ligation of two (or more) oligonucleotides in the presence of nucleic acid having the sequence of the resulting "di-oligonucleotide", thereby amplifying the di-oligonucleotide, may also be used in the amplification step of the present invention.

Following any amplification, it may be desirable to separate the amplification product from the template and the excess primer for the purpose of determining whether specific amplification has occurred. In one embodiment, amplification products are separated by agarose, agarose-acrylamide or polyacrylamide gel electrophoresis using standard methods (Sambrook et al., 1989).

Alternatively, chromatographic techniques may be employed to effect separation. There are many kinds of chromatography which may be used in the present invention: adsorption, partition, ion exchange and molecular sieve, and many specialized techniques for using them including column, paper, thin-layer and gas chromatography.

Amplification products must be visualized in order to confirm amplification of the marker sequences. One typical visualization method involves staining of a gel with ethidium bromide and visualization under UV light. Alternatively, if the amplification products are integrally labeled with radio- or fluorometrically-labeled nucleotides, the amplification products can then be exposed to x-ray film or visualized under the appropriate stimulating spectra, following separation.

In one embodiment, visualization is achieved indirectly. Following separation of amplification products, a labeled, nucleic acid probe is brought into contact with the amplified marker sequence. The probe preferably is conjugated to a chromophore but may be radiolabeled. In another embodiment, the probe is conjugated to a binding partner, such as an antibody or biotin, and the other member of the binding pair carries a detectable moiety.

In one embodiment, detection is by Southern blotting and hybridization with a labeled probe. The techniques involved in Southern blotting are well known to those of skill in the art and can be found in many standard books on molecular protocols (Sambrook et al., 1989). Briefly, amplification products are separated by gel electrophoresis. The gel is then contacted with a membrane, such as nitrocellulose, permitting transfer of the nucleic acid and non-covalent binding. Subsequently, the membrane is incubated with a chromophore-conjugated probe that is capable of hybridizing with a target amplification product. Detection is by exposure of the membrane to x-ray film or ion-emitting detection devices.

One example of the foregoing is described in U.S. Pat. No. 5,279,721, incorporated by reference herein, which discloses an apparatus and method for the automated electrophoresis and transfer of nucleic acids. The apparatus permits electrophoresis and blotting without external manipulation of the gel and is ideally suited to carrying out methods according to the present invention.

4.11 Biological Functional Equivalents

Modification and changes may be made in the structure of the polynucleotides and polypeptides of the present invention and still obtain a functional molecule that still possesses desirable characteristics. As mentioned above, it is often desirable to introduce one or more mutations into a specific polynucleotide sequence. In certain circumstances, the resulting encoded polypeptide sequence is altered by this mutation, or in other cases, the sequence of the polypeptide is unchanged by one or more mutations in the encoding polynucleotide.

When it is desirable to alter the amino acid sequence of a polypeptide to create an equivalent, or even an improved, second-generation molecule, the amino acid changes may be achieved by changing one or more of the codons of the encoding DNA sequence, according to Table 1.

For example, certain amino acids may be substituted for other amino acids in a protein structure without appreciable loss of interactive binding capacity with structures such as, for example, antigen-binding regions of antibodies or binding sites on substrate molecules. Since it is the interactive capacity and nature of a protein that defines that protein's biological functional activity, certain amino acid sequence substitutions can be made in a protein sequence, and, of course, its underlying DNA coding sequence, and nevertheless obtain a protein with like properties. It is thus contemplated by the inventors that various changes may be made in the polynucleotide sequences disclosed herein, without appreciable loss of their biological utility or activity.

TABLE 1

| Amino Acids | | | Codons | | | | |
|---|---|---|---|---|---|---|---|
| Alanine | Ala | A | GCA | GCC | GCG | GCU | |
| Cysteine | Cys | C | UGC | UGU | | | |
| Aspartic acid | Asp | D | GAC | GAU | | | |
| Glutamic acid | Glu | E | GAA | GAG | | | |
| Phenylalanine | Phe | F | UUC | UUU | | | |
| Glycine | Gly | G | GGA | GGC | GGG | GGU | |
| Histidine | His | H | CAC | CAU | | | |
| Isoleucine | Ile | I | AUA | AUC | AUU | | |
| Lysine | Lys | K | AAA | AAG | | | |
| Leucine | Leu | L | UUA | UUG | CUA | CUC | CUG | CUU |
| Methionine | Met | M | AUG | | | | |
| Asparagine | Asn | N | AAC | AAU | | | |
| Proline | Pro | P | CCA | CCC | CCG | CCU | |
| Glutamine | Gln | Q | CAA | CAG | | | |
| Arginine | Arg | R | AGA | AGG | CGA | CGC | CGG | CGU |
| Serine | Ser | S | AGC | AGU | UCA | UCC | UCG | UCU |
| Threonine | Thr | T | ACA | ACC | ACG | ACU | |
| Valine | Val | V | GUA | GUC | GUG | GUU | |
| Tryptophan | Trp | W | UGG | | | | |
| Tyrosine | Tyr | Y | UAC | UAU | | | |

In making such changes, the hydropathic index of amino acids may be considered. The importance of the hydropathic amino acid index in conferring interactive biologic function on a protein is generally understood in the art (Kyte and Doolittle, 1982, incorporate herein by reference). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like. Each amino acid has been assigned a hydropathic index on the basis of their hydrophobicity and charge characteristics (Kyte and Doolittle, 1982), these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is known in the art that certain amino acids may be substituted by other amino acids having a similar hydropathic index or score and still result in a protein with similar biological activity, i.e. still obtain a biological functionally equivalent protein. In making such changes, the substitution of amino acids whose hydropathic indices are within ±2 is preferred, those that are within ±1 are particularly preferred, and those within ±0.5 are even more particularly preferred. It is also understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain a biologically equivalent, and in particular, an immunologically equivalent protein. In such changes, the substitution of amino acids whose hydrophilicity values are within ±2 is preferred, those that are within ±1 are particularly preferred, and those within ±0.5 are even more particularly preferred.

As outlined above, amino acid substitutions are generally therefore based on the relative similarity of the amino acid side-chain substituents, for example, their hydrophobicity, hydrophilicity, charge, size, and the like. Exemplary substitutions which take several of the foregoing characteristics into consideration are well known to those of skill in the art and include: arginine and lysine; glutamate and aspartate; serine and threonine; glutamine and asparagine; and valine, leucine and isoleucine.

5.0 EXAMPLES

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

5.1 Example 1

Materials and Methods

Abbreviations used include: AAV, Adeno-associated virus; Ad, Adenovirus; HSV-1, Herpes simplex virus-1; MOI, multiplicity of infection; pfu, plaque-forming units; wt, wild type.

5.1.1 Cell Lines

HeLa cells were maintained in Dulbecco's modified Eagle's media (DMEM, Gibco-BRL, Grand Island, N.Y.) that contained 10% heat inactivated fetal calf serum (FCS). Vero cells were maintained in DMEM which contained 5% FCS. The V27 cell line, a neomycin resistant Vero cell line capable of expressing ICP27, was maintained in DMEM which contained 10% FCS and has already been described (Rice and Knipe, 1990). All 293 cell lines were maintained in DMEM which contained 10% FCS. Cells were cultured at 37° C. in 5% $CO_2$.

The UF2-293 cell line was generated by transfection of a 10 cm dish of 293 cells (from ATCC) with 10 μg of pUF2 DNA (Zolotukhin et al., 1996). The cells were then passaged in 600 μg/ml G418 (Gibco-BRL) for three weeks. Surviving cells were then sorted using fluorescence-activated cell sorting (FACS), utilizing the adsorption and emission spectrum of the humanized green fluorescent protein (hGFP) to isolate high expressing cells (Zolotukhin et al., 1996). Cells were considered high expressors when on adsorption of light of 395 nm wavelength, emitted light of 509 nm wavelength at an intensity 125 times greater than the emission of similarly stimulated, non-transfected 293 cells. The high expressors were maintained in G418 at 600 μg/ml.

The GFP-92 cell line was created by infecting 293 cells with rAAV-UF2. Cells were passaged in 200 μg G418 for two weeks and screened for GFP fluorescence. Colonies were isolated and analyzed by PCR™, as described below, for their ability to produce rAAV when transfected with pIM45 DNA and superinfected with adenovirus (Ad5). A producer cell line was identified and single clones were again isolated and analyzed for their ability to produce rAAV.

5.1.2 Plasmids

The plasmids pUF2, psub201, pIM45 and pRS5 have been previously described (Flotte et al., 1995; Pereira et al., 1997; Samulski et al., 1987; Zolotukhin et al., 1996). pUF2 is a bicistronic vector containing the human cytomegalovirus (HCMV) major immediate early (MIE) enhancer driving humanized green fluorescent protein (hgfp) and the HSV-1 thymidine kinase promoter driving a neomycin resistant gene inserted between AAV-2 ITRs. pRS5 and pIM45 are helper plasmids that supply Rep and Cap for generating rAAV. pAAV2 is a pKS based vector containing the AAV-2 genome. pAAV-lacZ is a HCMV MIE driven lacZ reporter construct inserted between AAV-2 ITRs.

pHSV-RC was used to generate the HSV-1 amplicons HSV-RC/KOS and HSV-RC/d27 and is a pUC19-derived vector (FIG. 1). The a-sequence contains the HSV-1 packaging signals and was cloned into the EcoRI site of pUC19. The oriS sequence contains an HSV-1 origin of replication (the internal SmaI fragment from the HSV-1 ori S) and was inserted at SmaI to generate pHSV. To create pHSV-RC, the rep and cap genes from AAV-2 were isolated from psub201 by an XbaI digest and cloned onto the XbaI site of pHSV (FIG. 1).

pHSV-gfp was constructed from pHSV and p1.1-gfp (a vector expressing the green fluorescent protein (GFP). p1.1-gfp was NotI digested and Klenow blunted. This fragment was then cloned into the SphI digested and T4 polymerase blunted pHSV to create pHSV-gfp. p43-hgfp is based on the pUF2 vector. The expression cassette from pCI (isolated by a BamHI-BglII digest) was cloned between the ITRs of BglII digested pUF2 to create p43. The hgfp cDNA was isolated from pUF2 by a NotI digest and then cloned into the NotI site of the p43 to create p43-hgfp. pCI-hgfp was created by cloning hgfp into the NotI site of pCI. The 115 base pair deletion vector pCI-hgfpd was created by PflMI and PvuII digestion of pCI-hgfp, followed by T4 polymerase blunting of the overhanging ends, and then self-ligation of the vector.

5.1.3 Transfection

Transfections for the rescue of rAAV genomes from pAAV-lacZ were performed using Lipofectamine (Gibco- BRL), following the manufacturer's protocol 24 h after seeding 2×10⁵ HeLa cells onto 6 well plates. The UF2-293 cell line was generated by plating 1×10⁶ 293 cells onto a 10-cm dish followed by transfection with 10 μg of pUF2. This transfection was done by precipitation of plasmid DNA with $CaCl_2$ in 2× N,N-bis(2-hydroxyethyl)-2-aminoethanesulfonic acid (BES), (25 mM, pH 6.95). The transfected cells were incubated at 35° C., 3% $CO_2$ overnight. The transfected cells were rinsed once with phosphate buffered saline (PBS, pH 7.4) and grown in DMEM with 10% FCS. The GFP-92 cell line was created by seeding 1×10⁶ 293 cells on a 10 cm plate followed by transfection with 10 μg of pUF2 DNA by $CaCl_2$ coprecipitation in HEPES buffered saline. To generate the first passage of the amplicons HSV-RC/KOS and HSV-GFP/KOS, 1×10⁶ Vero cells were plated onto 10 cm dishes followed by transfection with 10 μg of pHSV-RC and 10 μg of HSV-1 (KOS) DNA or 10 μg of pHSV-gfp and 10 μg of HSV-1 (KOS) DNA by BES coprecipitation. To generate the first passage HSV-RC/d27, 1×10⁶ V27 cells were plated onto 10 cm dishes and transfected 24 h later with 20 μg of pHSV-RC DNA using Lipofectamine. To produce rAAVUF2 from the GFP-92 cells by transfection, 2×10⁶ cells were plated onto a 10 cm dish and transfected with 8 μg of pRS5 DNA using Lipofectamine.

5.1.4 Virus

HSV-1 (wt KOS strain) was propagated by infecting Vero cells (90% confluent in T175 flasks) at a multiplicity of infection (MOI) of 0.1 per cell. Adsorption of virus was done for 45 min in reduced serum DMEM (2% FCS). After full cytopathic effect (CPE) was observed (usually 48 h post infection) the cell pellet was collected by centrifugation (1000 rpm for 10 min), then frozen and thawed 3 times. Cell debris was removed by centrifugation (3000 rpm for 5 min). d27-1 is an ICP27 deletion of HSV-1 (KOS strain) and has been previously described (Rice and Knipe, 1990). d27-1 (ATCC PTA-4004) was propagated as described for HSV-1 except that the complementing cell line, V27 (ATCC PTA-4296), was used. Ad5 (from the American Type Culture Collection, Rockville, Md.) was propagated by infecting 293 cells (90% confluent in 15 cm dishes) at an MOI of 0.1 per cell. Ad5 was harvested as described for HSV-1 after full CPE was observed (usually 72 to 96 h post infection). AAV-2 was propagated by coinfection of 293 cells with AAV-2 (MOI of 200 particles per cell) and Ad5 (MOI of 0.1). AAV-2 viral lysates were prepared by freeze-thaw, and the Ad5 was heat inactivated by incubation at 55° C. for 45 min. HSV-1 (wt KOS) was titered by plaque forming assay on Vero cells. d27-1 was titered by plaque forming assay on V27 cells. Analysis of d27-1 stocks for the presence of wt HSV-1 was done by plaque assay on non-complementing Vero cells (<100 pfu/ml detected). Ad5 was titered by plaque forming assay on 293 cells. AAV-2 was titered for particles by dot blot analysis as described below for recombinant genomes in the amplicon stocks.

"Subject cultures of the invention have been deposited under conditions that assure that access to the cultures will be available during the pendency of this patent application to one determined by the Commissioner of Patents and Trademarks to be entitled thereto under 37 C.F.R. §§1.14 and 1.801 and 35 U.S.C. Å122. The deposits are available as required by foreign patent laws in countries wherein counterparts of the subject application, or its progeny, are filed. However, it should be understood that the availability of a deposit does not constitute a license to practice the subject invention in derogation of patent rights granted by governmental action.

The subject culture deposits will be stored and made available to the public in accord with the provisions of the Budapest Treaty for the Deposit of Microorganisms, i.e., they will be stored with all the care necessary to keep them viable and uncontaminated for a period of at least five years after the most recent request for the finishing of a sample of the deposit, and in any case, for a period of at least 30 (thirty) years after the date of deposit or for the enforceable life of any patent which may issue disclosing the cultures. The depositor acknowledges the duty to replace the deposits should the depository be unable to furnish a sample when requested, due to the condition of the deposits. All restrictions on the availability to the public of the subject culture deposits will be irrevocably removed upon the granting of any patent disclosing them.

Recombinant herpes simplex virus rHSV d27.1rc was deposited Feb. 1, 2002, and the host cell line V27 was deposited May 7, 2002 in the permanent collection of the American Type Culture Collection, 10801 University Blvd., Manassas, Va., 20110-2209, USA, under the terms of the Budapest Treaty. The required certificate of viability for rHSV d27.1 was issued by the ATCC on Aug. 2, 2002, and the strain accorded accession number ATCC PTA-4004. The required certificate of viability for V27 was issued by the ATCC on May 21, 2002, and the strain accorded accession number PTA-4296."

HSV-RC/KOS was propagated by harvesting the cell pellet by centrifugation (1000 rpm for 10 min) after full CPE was observed in the transfected cells. The cell pellet was frozen and thawed three times and cell debris removed by centrifugation (3000 rpm for 5 min). One fourth of the virus was then used to infect Vero cells (90% confluent in T175 flasks) as previously described to generate the second passage of HSV-RC/KOS. One fourth of the virus was used to infect Vero cells in T175 flasks to generate each successive passage. HSV-RC/d27 was generated by superinfection of the pHSV-RC transfected V27 cells with d27-1 virus 36 h post transfection at an MOI of 2.5. The cell pellet was collected as previously described after full CPE was observed (72 h post infection). Successive passages of HSV-RC/d27 were generated as described for HSV-RC/KOS except that the complementing cell line, V27, was used. Fourth passage or greater amplicon stocks were used in the studies described.

Each amplicon stock was titered for the presence of helper virus by a plaque-forming assay on the appropriate cell line (Vero cells for HSV-RC/KOS, V27 cells for HSV-RC/d27). The titers of HSV-1 in HSV-RC/KOS, in passages 2 through 6, varied between 1×10⁸ and 3×10⁸. The titer of d27-1 in HSV-RC/d27, in passage 2 through 5, varied between 1×10⁷ and 3×10⁷ pfu/ml. HSV-RC/d27 was analyzed for the presence of wt HSV-1 by plaque assay on non-complementing Vero cells (<100 pfu/ml detected). The titer of recombinant genomes (the rep and cap genome from pHSV-RC) in each amplicon stock was determined by dot blot analysis of the stocks. Aliquots of the virus were DNAseI treated for 2 h at 37° C. in DNAseI buffer (final concentration 10 mM Tris (pH 7.4), 10 mM KCl, 1.5 mM $MgCl_2$) and then proteinase K treated for 2 h at 55° C. in proteinase K buffer (final concentration 10 mM Tris (pH 7.4), 5 mM EDTA, 0.5% SDS). 5 μl of 5N NaOH was then added to the samples and they were incubated at 65° C. for 1 h. The samples were neutralized with 50 μl of 2N $NH_4OH$ and were then transferred using a vacuum apparatus to a nylon membrane that was first equilibrated with 1N $NH_4OH$ for 1 h. The slots were then washed with 50 μl of 2N $NH_4OH$. A standard curve of serial dilutions of HSV-1 was processed and applied to the membrane in an identical fashion.

A standard curve of serial dilutions of pHSV-RC was denatured, neutralized and also applied to the membrane.

The membrane was then incubated with prehybridization solution (1% SDS, 5 mg/ml nonfat dried milk, 0.05 mg/ml heparin, 0.2 mg/ml denatured salmon sperm DNA, 60 mg/ml PEG 8000, 5×SSPE (750 mM NaCl, 50 mM $Na_2HPO_4$, 5 mM EDTA, and 10% formamide) for 4 h at 60° C. The membrane was hybridized overnight at 60° C. in the prehybridization solution with [$\alpha$-$^{32}$P] dATP labeled, random primer generated probe. The probe was generated from a 2.1 kb cap fragment isolated by KpnI digestion of psub201. After hybridization, the membrane was then washed twice in 0.1×SSC and 0.1% SDS at 65° C. for 45 min. The membrane was exposed to film for 24–48 h at –70° C. The titer of recombinant genomes varied between $3\times10^7$ to $7\times10^7$ recombinant genomes per ml for HSV-RC/KOS and $1\times10^7$ to $3\times10^7$ recombinant genomes per ml for HSV-RC/d27. The specificity of the probe for recombinant genomes and not HSV-1 genomes was confirmed by demonstrating that the HSV-1 standard curve did not produce a signal when the membrane was hybridized with probe for the recombinant genomes. To verify that the HSV-1 DNA did transfer, the membrane was stripped by washing the membrane with 0.1×SSC and 0.1% SDS at 100° C. and then rehybridized with an [$\alpha$-$^{32}$P] dATP labeled oriS DNA probe. The membranes were then processed as described above.

The packaging, purification and titering of rAAVlacZ has been described previously (Kessler et al., 1996). rAAVUF2 was prepared from six T175 flasks of UF2-293 cells. Flasks were infected with HSV-RC/KOS (MOI of the HSV-RC/KOS was 2 recombinant genomes per cell and 2.5 pfu of HSV-1 per cell) when the cells were 90% confluent ($10^8$ cells). The total number of cells in the preparation was determined by counting the number of cells present on a similarly prepared flask using a hemocytometer. 48 h later (after full CPE), the cells were centrifuged for 10 min at 1000 rpm. The cell pellet was then frozen and thawed three times and cell debris was removed by centrifugation at 3000 rpm for 10 min. The sample was heat inactivated for 1 h at 55° C. and DNAseI treated for 1 h at 37° C. in DNAse buffer. Virus was purified on an isopycnic CsCl gradient as described (Kessler et al., 1996). 100 µl fractions were collected, the refractive index was determined for each fraction, and each fraction was then analyzed for the presence of rAAVUF2 by infecting HeLa cells in the presence of Ad5 and directly observing the cells by fluorescent microscopy for the presence of hGFP expression 36 h later. $2\times10^5$ HeLa cells were plated onto 6 well dishes 24 h before coinfection with 1 µl of each CsCl fraction and Ad5 (MOI of 2). Positive fractions were pooled and dialyzed overnight against 4 l of 10 mM Tris, 1 mM EDTA (pH 7.4). The presence of infectious rAAVUF2 was determined by replication assay as described below. No contaminating HSV-1 was detected in a Vero cell plaque assay with a sensitivity of detection greater than 100 pfu/ml.

rAAVUF2 was prepared from GFP-92 cells by one of three methods. Thirty 10 cm plates were seeded with $2\times10^6$ cells, and 24 h later the cells were either transfected with pRS5 as described above or infected with HSV-RC/d27 (MOI of the HSV-RC/d27 was one recombinant genome per cell and one pfu of d27-1 per cell). The total cell number in each preparation was determined by counting the cells on identically seeded plates using a hemocytometer. For the transfection method, the transfection solution was removed 8 h later and Ad5 (MOI of 2.5) was added to the cells in DMEM with 10% FCS. One group of plates that was infected with HSV-RC/d27 was superinfected with wt HSV-1 (MOI of 1) 12 h later. The cells were collected after full CPE had developed and processed as described above.

5.1.5 Replication Assays

Rescue and replication of rAAV genomes from transfected plasmids, producer cell lines or infected rAAV particles was demonstrated by first seeding $2\times10^5$ HeLa cells onto 6 well plates or $1\times10^6$ HeLa cells onto 10 cm dishes. After 24 h, the cells were either mock transfected, mock infected, transfected with a rAAV plasmid, infected with AAV-2, infected with rAAV virus or a combination of these (as described in the brief description of the figures). After an additional 24 h, the cells were either mock infected, infected with HSV-1, infected with d27-1, or infected with one of the amplicons (as described in the brief description of the figures). Cells were harvested 36 h later and centrifuged for 5 min at 2000 rpm. Media was removed and small molecular weight DNA was isolated from the pellet by Hirt extraction (Hirt, 1967). 10 µg of Hirt extracted DNA was loaded per lane on a 0.5% agarose gel and run for 12 h at 25V. DNA from the gel was transferred to a nylon membrane by Southern blotting. The nylon membrane was then prehybridized and hybridized and as described above. The different templates used to generate the [$\alpha$-$^{32}$P] dATP labeled probes were a 3.3-kb lacZ DNA fragment, a 4.4-kb AAV-2 DNA fragment, and a 700-bp hgfg DNA fragment. The membranes were stripped as described above and reprobed for the presence of replicating wt AAV genomes using an [$\alpha$-$^{32}$P] dATP-labeled 2.1-kb cap fragment (isolated by KpnI digestion of psub201). For the DpnI assay, 10 µg of Hirt extracted DNA was extensively digested with DpnI (100 U) for 24 h, ethanol precipitated and run on a 0.8% agarose gel for 12 h at 25V.

5.1.6 PCR™ Assays

Samples from clarified cell lysates (70 µl from 7 ml for detection of rAAVUF2 made from the cell line UF2-293 with HSV-RC/KOS, 2 µl from 3 ml for detection of rAAVUF2 made from the GFP-92 cell line with HSV-RC/d27, 100 µl from 3 ml for wt AAV detection) were treated with 50 U DNAseI for 2 h at 37° C. in DNAseI buffer and then proteinase K digested in proteinase K buffer for 2 h at 55° C. The samples were then phenol and chloroform extracted and ethanol precipitated followed by centrifugation at 14,000 rpm for 30 min at 4° C. to pellet the DNA. The DNA pellet was rinsed once with 70% ethanol, then dried, and reconstituted in $dH_2O$. An aliquot of this sample (1 µl from 20 µl for rAAVUF2 and 9 µl of 10 µl for wt AAV) was used in the PCR™ reactions. PCR™ reactions were carried out in a 50-µl volume, and PCR™ products (15 µl) were analyzed on 2% agarose gels at 100V. For the quantitative-competitive PCR™ (QC-PCR™), the products were analyzed on 2% agarose gels for 3 h at 50V. A Stratagene Eagle Eye™ detection system was used to record the images.

The primers used to detect rAAVUF2 particles anneal to the coding region of hfgp and generate a 700 bp product. The hgfp sense primer was 5'-ATGAGCAAGGGC GAGGAACTGTTC-3' (SEQ ID NO:1). The hgfp antisense primer was 5'-TCACTTGTACAGCTCGTCCATGCC-3' (SEQ ID NO:2). The positive control was 200 pg of p43-hgfp. The PCR™ conditions were: 4 min at 94° C.; 25 cycles of 60 seconds at 94° C., 30 seconds at 60° C., 60 seconds at 72° C.; and then 4 min at 72° C.

The primers used to detect the presence of wt AAV anneal to the ITR D sequence and to the cap coding sequence and generate a 370 bp product. The D sequence primer was 5'-CTCCATCACTAGGGGTTCC-3' (SEQ ID NO:3). The cap primer was 5'-CTTCATCACACAGTACTCCACGGG-3' (SEQ ID NO:4). The positive controls were serial dilutions of pAAV2. The PCR™ conditions were identical to those used with the hgfp primers except that 30 cycles were completed. Typically 10 fg of pAAV2 could be detected by PCR™ amplification after ethidium bromide staining.

A particle count of rAAVUF2 was determined by QC-PCR™ and was based on the determination of the amount of rAAVUF2 template present in a sample through comparison with a known quantity of internal control standard. The internal control for the QC-PCR™ reactions, pCI-hgfpd, was identical to the hgfp sequence to which the primers annealed and amplified except that an internal deletion was made as described above. The hgfp primers generate a 585 bp product when pCI-hgfpd is used as the template. A constant amount of rAAVUF2 DNA was added to each QC-PCR™ reaction (1 µl) and the amount of internal control was varied to produce a standard curve (see brief description of the figures for exact amounts of pCI-hgfpd added to each reaction). The amount of rAAVUF2 template present was then determined by identifying the amount of internal control DNA that had to be added which would give full size and deleted PCR™ products of equal intensity after ethidium bromide staining. The number of single strand template genomes present (the number of particles) was then calculated.

The PCR™ detection of rAAVUF2 particles does not give a false positive result under the conditions used. As a negative control for the specificity of the PCR™ analysis to detect actual rAAV particles and not residual DNA template from undigested cellular DNA, $1 \times 10^8$ GFP-92 cells were pelleted and reconstituted in 1 ml of DMEM. The cells were then frozen and thawed three times. The cell debris was removed by centrifugation at 3000 rpm for 10 min and DMEM was added to the lysate so that the final volume was 1 ml. 100 µl of this sample was DNAseI and proteinase K treated, phenol and chloroform extracted, precipitated and reconstituted in 20 µl dH$_2$O. 5 µl (out of 20 µl) of the negative control did not give a detectable PCR™ product when the hgfp primers and PCR™ conditions that were used for all hgfp PCR™ reactions were employed for thirty amplification cycles.

5.2 Example 2

Construction of HSV-1 Amplicon which Contains Rep, an HSV-1 Origin of Replication and HSV-1 Packaging The expression of Rep 78 or 68 has been shown to inhibit the replication of DNA viruses. Rep interacts with Ad and cellular DNA replication in viral replication centers and disrupts their subsequent formation and function (Weitzman et al., 1996a, 1996b). Expression of the Rep protein also inhibits HSV-1 induced cellular DNA amplification and HSV-1 viral DNA replication itself (Heilbronn et al., 1990).

It was considered possible that the expression of Rep interfered with HSV-1 DNA replication to such an extent that creation of amplicon stocks of reasonable titer would not be possible. Similar problems were previously observed by multiple investigators attempting to create a recombinant Ad vector expressing Rep.

To determine if an amplicon system that expressed Rep could be created, a plasmid that expresses Rep from the p5 and p19 promoters was constructed, pHSV-RC (FIG. 1). When pHSV-RC was cotransfected with HSV-1 (KOS) DNA into Vero cells, it took 48 h longer for induction of full CPE than when HSV-1 DNA and pUC19 or when HSV-1 DNA and pHSV-gfp (a non-Rep expressing control amplicon plasmid) were transfected (7 days for full CPE vs. 5 days). In subsequent passages (P2–P6), no difference was seen in the time course of CPE for the different amplicon stocks (48 h for full CPE). Also, the titers of plaque forming HSV-1 and recombinant genomes in the different passages did not vary a great deal (HSV-1 titer varied from $1 \times 10^8$ to $3 \times 10^8$ pfu/ml, recombinant genome dot blot titer varied from $3 \times 10^7$ to $7 \times 10^7$ genomes/ml.

5.3 Example 3

Rescue and Replication or rAAV Genome is Supported by HSV-1 Amplicon Expressing Rep from the P5 and P19 Promoters and Made with HSV-1 Helper Virus (HSV-RC/KOS)

The HSV-1 amplicon had to be able to rescue and replicate rAAV genomes efficiently if the HSV-1 amplicon system expressing Rep and Cap were to be successful at packaging rAAV genomes into virions. Rescue and replication of rAAV genomes by HSV-RC/KOS requires the appropriate expression of Rep from the p5 and p19 promoters, which are in a different genomic structural context than they are in the wt AAV genome. Additionally, expression of Rep from the amplicon genome has to be appropriately timed with HSV-1 early gene expression so that rAAV replication proceeds, as does wt AAV replication.

The ability of HSV-RC/KOS to replicate rAAV genomes introduced into cells by infection of rAAV virions, by transfection as plasmids, or when maintained as proviral rAAV genomes integrated into cellular chromosomal DNA was analyzed.

The ability of HSV-RC/KOS to replicate and amplify a rAAV genome (rAAVlacZ) after rAAV infection was examined. HeLa cells ($2 \times 10^5$) were seeded onto 6 well plates. After 24 h, the cultures were either mock infected, infected with rAAVlacZ ($5 \times 10^4$ particles), AAV-2 (MOI of 1000 particles per cell) or both. The cells were infected with HSV-1 (KOS strain, MOI of 2), or HSV-RC/KOS (MOI of the HSV-RC/KOS was one recombinant genome per cell and 2 pfu of HSV-1 per cell) 24 h later. The wells were scraped and the cells were collected and centrifuged (2000 rpm, 5 min) after 36 h. Media was removed and the small molecular weight DNA in the pellet was isolated by Hirt extraction. Hirt extracted DNA (5 µg) was loaded per lane on a 0.8% agarose gel and run for 12 h at 25V. DNA from the gel was transferred to Nylon membrane by Southern blotting, and probed with an [α-$^{32}$P] dATP-labeled lacZ DNA probe or an [α-$^{32}$P] dATP-labeled psub201 DNA probe.

In this assay, replicative intermediates of rAAV, the double stranded monomers ($RF_m$), double stranded dimers ($RF_d$), and higher molecular weight replicative forms, indicate successful replication. Positive replication was observed in samples in which small molecular weight DNA was analyzed from cells coinfected with rAAV, AAV-2 and HSV-1 (positive control) or coinfected with rAAV and HSV-RC/KOS. Replicative forms of rAAV were not detectable in any of the other samples.

These data illustrate that HSV-1 gene expression and Rep expression from an HSV-1 amplicon is temporally and quantitatively appropriate for the task of replicating rAAV genomes introduced into cells by viral infection. In addition, the intensity of the $RF_m$ and $RF_d$ in cells coinfected with rAAV and HSV-RC/KOS, as compared to cells coinfected with rAAV, AAV-2 and HSV-1, suggests that Rep expression from an amplicon in the presence of HSV-1 coinfection is capable of supporting rAAV replication at a higher level than AAV-2 and HSV-1 at similar multiplicities of infection. This may be due to the absence of replication competent AAV-2 in HSV-RC/KOS. Replication competent AAV-2 would successfully compete with rAAV for replication machinery and lead to a decrease in rAAV replication (Clark et al., 1996).

These results also demonstrate that wt AAV is not generated and amplified by an HSV-1 amplicon expressing Rep protein. The $RF_m$ and $RF_d$ of wt AAV were only observed in the samples in which Hirt extracted DNA was analyzed from cells coinfected with AAV-2 and HSV-1 and probed for rep and cap sequences. In addition, a 7-day exposure of the Southern blot did not reveal any replicative forms of wt AAV in any additional samples. Normally, replication of wt AAV replicative forms is observable after 48 h exposure of the Southern blot.

The ability of HSV-RC/KOS to rescue and replicate rAAV genomes from different rAAV templates was also evaluated. These data indicate that HSV-RC/KOS was able to rescue and replicate rAAV genomes from transfected plasmids. HeLa cells were seeded onto 6 well plates ($2 \times 10^5$). The cells were either mock transfected, transfected with 3 µg of pAAVlacZ, or infected with rAAVlacZ ($5 \times 10^4$ particles) 24 hours later. The plasmid pAAVlacZ contains a HCMV MIE driven lacZ expression cassette flanked by ITRs. The cells were either mock infected, infected with wt HSV-1 (MOI of 2) or infected with HSV-RC/KOS (MOI of the HSV-RC/KOS was one recombinant genome per cell and 2 pfu of HSV-1 per cell) 24 h later. Cells were collected 36 h later and centrifuged for 5 min at 2000 rpm. Media was removed and small molecular weight DNA was isolated from the pellet by Hirt extraction. Hirt extracted DNA (10 µg) was extensively digested with DpnI (100 U) for 24 h. DpnI does not digest newly replicated rAAV, which is not methylated after replication in eukaryotic cells. The DNA was then ethanol precipitated and analyzed on a 0.8% agarose gel for 12 h at 25V. DNA was transferred to a nylon membrane by Southern blotting. The membrane was hybridized with an [$\alpha$-$^{32}$P] dATP-labeled lacZ DNA probe and exposed to film for 24 h.

The $RF_m$ and $RF_d$ were readily observed the positive control for rescue and replication of rAAV genomes. Rescue and replication of DpnI resistant rAAV genomes from transfected plasmids was also observed where pAAVlacZ transfection was followed by HSV-RC/KOS superinfection. Replicative forms of rAAV were not observed in any of the other samples.

HSV-RC/KOS was also proven to rescue and amplify proviral rAAV genomes that were chromosomally integrated in the cell line UF2-293. Plates (10 cm) were seeded with $1.5 \times 10^6$ UF2-293 cells. The cells were mock infected, infected with HSV-1 (MOI of 2) or infected with HSV-RC/KOS (MOI of the HSV-RC/KOS was one recombinant genome per cell and 2 pfu of HSV-1 per cell) 24 h later. Plates were scraped 36 h post infection. Cells were centrifuged (5 min, 2000 rpm) and the media was discarded. Small molecular weight DNA was isolated from the pellet by Hirt extraction. Hirt extracted DNA (10 µg) was analyzed per well on a 0.8% agarose gel for 12 h at 25V. DNA was transferred to a nylon membrane by Southern blotting. The membrane was hybridized with an [$\alpha$-$^{32}$P] dATP-labeled hgfp DNA probe, and exposed to film for 24 hours.

The replicating monomers and dimers indicative of rAAV rescue and replication were only seen in the sample containing Hirt extracted DNA from the UF2-293 cells infected with HSV-RC/KOS. Rescue of rAAV genomes from the UF2-293 cells was not due to latent wt AAV infection of the cells, which could supply Rep in trans. Replicative forms of rAAV were not observed in the sample in which Hirt extracted DNA was analyzed from HSV-1 infected UF2-293 cells. If the UF2-293 cells were latently infected with wt AAV, rescue and replication of rAAV genomes would be observed in this sample. In addition, stripping of the membrane and reprobing for wt AAV replicative forms with an [$\alpha$-$^{32}$P] dATP-labeled cap probe did not reveal any wt AAV replicative forms after exposure of the Southern blot for 7 days. HSV-RC/KOS was also able to rescue and replicate rAAV proviral genomes from GFP-92 cells in a similar assay with similar controls for detecting the presence of wt AAV replication.

5.4 Example 4

HSV-RC/KOS Successfully Replicates and Packages rAAV at Low Efficiency

To determine if HSV-RC/KOS could replicate and package rAAV particles, and measure the efficiency of the process, the particle titers of rAAVUF2 were determined by QC-PCR™ of the rAAVUF2 prepared from UF2-293 cells using HSV-RC/KOS. UF2-293 cells ($1 \times 10^8$) were infected with HSV-RC/KOS. After full CPE occurred, the cell pellet was harvested, then frozen and thawed three times. The cell lysate was then clarified and an aliquot (1/100th of the volume of the cell lysate) was treated with DNAseI and proteinase K, phenol and chloroform extracted and precipitated in ethanol. Aliquots (1 µl) of the reconstituted DNA pellet (1/20th of the volume) were then analyzed by QC-PCR™.

For the controls, either no DNA template, 100 pg p43-hgfp, 1 µl of rAAVUF2 DNA, or 50 pg of pCI-hgfpd was added to the reaction mixture. For the QC-PCR™ reactions 1 µl of viral template and various amounts of internal control DNA template (pCI-hgfpd) were added to each PCR™ reaction. The amount of internal control template was 5 pg, 1 pg, 500 fg, 100 fg, or 20 fg. A 1-kb marker was run on the gel as a molecular weight standard.

The number of particles produced per cell was 2.3+/−0.3. The number of rAAVUF2 particles produced per cell was 100 fold lower than the number of particles usually produced per cell by transfection methods employing adenovirus superinfection.

5.5 Example 5

HSV-1 Amplicon Expressing Rep and Cap from the P5 and P19 Promoters and Made with D27-1 Helper Virus (HSV-RC/D27) Supports Rescue and Replication of rAAV Genomes The efficient replication of rAAV genomes in a lytic cycle by HSV-RC/KOS is clearly shown, as described above. Packaging of rAAV genomes by HSV-RC/KOS is extremely inefficient, however. The initial choice of wt HSV-1 as helper virus to generate HSV-RC/KOS was made because it can supply the necessary functions (early gene expression) required for wt AAV production Unfortunately, HSV-1 induces CPE in infected cells much more rapidly than a similar infection with Ad. The rapid time course of host cell death probably limits the amount of rAAV that can be produced from each cell. Full CPE of host cells was consistently observed within 36 to 48 h after infection with HSV-1 compared to 72 to 96 h after adenoviral infection at the same MOIs. The rapidity of CPE after HSV-1 infection is due, in part, to the toxicity of the HSV-1 immediate early gene products, which are expressed within two h after infection and quickly alter the host cell's macromolecular synthesis machinery (Johnson et al., 1992a; Johnson et al., 1994). Host cell transcription, RNA splicing and protein synthesis are all perturbed by immediate early gene products of HSV-1 and contribute to the rapid CPE (Johnson et al., 1992a; Johnson et al., 1994).

An additional possible reason for the inefficiency of rAAV particle production by HSV-RC/KOS is the inhibition of host cell mRNA splicing by ICP27 (Sandri-Goldin and Mendoza, 1992). ICP27 expression would also interfere with the appropriate splicing of the AAV late p40 tanscripts, which encode Cap. Decreased synthesis of Cap message in turn would limit the production of rAAV.

In order to increase the yield of rAAV produced per cell, a Rep and Cap expressing amplicon was made using the defective HSV-1 virus, d27-1. The virus d27-1 has a deletion in ICP27. Although the other immediate early proteins are expressed in d27-1 and the vector induces CPE, ICP27 itself is toxic to cells and therefore elimination of ICP27 was expected to reduce toxicity of the defective vector compared to HSV-1 (Johnson et al., 1994). The ICP27 protein is also implicated in the inhibition of mRNA splicing, and the d27-1 strain should permit more efficient and accurate splicing of the late p40 transcripts encoding Cap and increase rAAV particle yield per cell. In addition, ICP 27 is involved in the down regulation of HSV-1 early gene expression. ICP27 mutants overexpress the early gene products of HSV-1, such as ICP8, and it is these early gene products that are essential for wt AAV productive infection (McCarthy et al., 1989; Rice and Knipe, 1990; Weindler and Heilbronn, 1991). Overexpression of early gene products may result in an increase in the yield of rAAV particles produced.

To determine if an HSV-1 amplicon expressing Rep and Cap and made with d27-1 helper virus could support replication and packaging of rAAV particles, HSV-RC/d27 was produced and tested in a replication assay. Dishes were seeded with $2 \times 10^5$ GFP-92 cells per well. After 24 h the cells were mock infected, infected with wt HSV-1 (MOI of 1), infected with d27-1 (MOI of 1), infected with HSV-RC/d27 (MOI of the HSV-RC/d27 was 1 recombinant genome per cell and 1 pfu of d27-1 per cell), or infected with HSV-RC/d27 (MOI of the HSV-RC/d27 was one recombinant genome per cell and one pfu of d27-1 per cell) and 12 h later superinfected with HSV-1 (MOI of 1). Plates were scraped 36 h post infection. Cells were centrifuged (5 min, 2000 rpm) and the media was discarded. Small molecular weight DNA was isolated from the pellet by Hirt extraction. Hirt extracted DNA (10 µg) was analyzed per well on a 0.8% agarose gel for 12 h at 25V. DNA was transferred to a nylon membrane by Southern blotting. The membrane was hybridized with an $[\alpha\text{-}^{32}P]$ dATP-labeled hgfp DNA probe, and exposed to film for 24 hours.

The capability of HSV-RC/d27, alone, to rescue and replicate chromosomally integrated rAAV provirus from the cell line GFP-92 was demonstrated. Coordinated expression of Rep from the amplicon and early genes from d27-1 allows replication of rAAV. Wild type levels of HSV-1 DNA synthesis and HSV-1 late gene expression are clearly not required for rAAV replication, in agreement with previous reports (Weindler and Heilbronn, 1991). Addition of HSV-1, which would provide ICP27 and allow HSV-1 DNA replication and expression of late genes to occur, does increases the amount of rAAV DNA replication.

To analyze if HSV-RC/d27 was sufficient not only to replicate but also to package rAAV in the absence of wt levels of HSV-1 DNA synthesis and late gene expression, the ability of the HSV-RC/d27 amplicon to generate rAAVUF2 DNAseI resistant particles from the cell line GFP-92 was studied. GFP-92 cells ($2 \times 10^5$) were plated onto 6 well dishes. After 24 h, the cells were either not infected nor transfected, infected with Ad5 (MOI of 2), HSV-1, (MOI of 1), d27-1 (MOI of 1), HSV-RC/d27 (MOI of the HSV-RC/d27 was one recombinant genome per cell and one pfu of d27-1 per cell), or transfected with pRS5 DNA (which supplies Rep and Cap; 2 µg) and superinfected with Ad5 eight h later (MOI of 2). The cells were scraped and pelleted after full CPE was observed. The cell pellet was then frozen and thawed three times in 100 µl DMEM and clarified. An aliquot of the clarified lysate (10 µl) was then DNAseI and proteinase K treated, phenol and chloroform extracted and ethanol precipitated. The DNA was pelleted and reconstituted in 20 µl dH$_2$O. An aliquot (2 µl) was then added to 50 µl PCR™ reactions. Aliquots of the PCR™ products (15 µl) were analyzed on a 2% agarose gel at 100V for 30 min. For the controls, either no DNA template or 200 pg p43-hgfp was added to the PCR™ reaction. A 1-kb marker was run on the gel as a molecular weight standard.

HSV-RC/d27, alone, was sufficient to produce DNAseI resistant, PCR™ detectable rAAV genomes from rAAVUF2 particles. These data support the report that neither HSV-1 DNA synthesis, nor late gene expression, is necessary for efficient AAV-2 particle production (Weindler and Heilbronn, 1991).

The CMV92gfp cell line was not latently infected with wt AAV as demonstrated by the absence of $RF_m$ and $RF_d$ in the study described above. If GFP-92 cells were latently infected with wt AAV, replication of rAAV genomes would have occurred when the cells were infected with HSV-1 or d27-1 alone. In addition, replicative forms of wt AAV were not detected when the membrane was stripped and probed for wt AAV sequences with an $[\alpha\text{-}^{32}P]$ dATP-labeled cap DNA probe after a 7 day exposure. In addition, no PCR™ detectable rAAV genomes were present after the cells were infected with any of the control viruses (Ad5, HSV-1 or d27-1).

5.6 Example 6

HSV-RC/D27 Replicates and Packages rAAV as Efficiently as Standard Methods

To determine if HSV-RC/d27 could package rAAV as efficiently as transfection methods, larger scale production of rAAVUF2 was attempted. GFP-92 cells (at 60% confluency) were either transfected with pRS5 (and then superinfected with Ad5), or infected with HSV-RC/d27 (with and without superinfection with HSV-1). $6 \times 10^7$ GFP-92 cells were in each preparation. After full CPE occurred, the cell pellet was harvested, frozen, and thawed three times. The cell lysate was then clarified and an aliquot (¹⁄₁₅₀₀th of the volume of the cell lysate) was treated with DNAseI and proteinase K, phenol and chloroform extracted and precipitated in ethanol.

Aliquots of the reconstituted DNA pellet (1 µl, ¹⁄₂₀th of the total volume) were then analyzed by QC-PCR™ to determine the number of particles produced per cell by each of the methods. For the controls, either no DNA template, 100 pg p43-hgfp, 1 µl of rAAVUF2 DNA, or 50 pg of pCI-hgfpd was added to the reaction mixture. For the QC-PCR™ reactions 1 µl of viral template and various amounts of internal control DNA template (pCI-hgfpd) were added to each PCR™ reaction The amount of internal control template was 100 pg, 25 pg, 5 pg, 1 pg, or 200 fg. A 1 kb marker was run on the gel as a molecular weight standard.

The particle production for the various methods from two independent preparations of amplicons is listed in Table 2.

The data indicate that HSV-RC/d27 is almost as effective as transfection methods at producing rAAV. The yield of rAAV can be further increased by the addition of HSV-1 to the amplicon HSV-RC/d27 for the final 24 h of cell growth. The studies were done at 60% cellular confluence 24 h after seeding to maximize transfection efficiency. Cell confluency can likely be increased to 90%, as would be done during rAAV production with these amplicons, without affecting the yield per cell, thereby improving overall yield and reducing cost.

TABLE 2

EFFICIENCY OF RAAV PRODUCTION

| Method | Total Cells | Preparation 1 | | Preparation 2 | |
|---|---|---|---|---|---|
| | | Total Particles | Particles/Cell | Total Particles | Particles/Cell |
| Transfection | $6.5 \times 10^7$ | $2.4 \times 10^{10}$ | 400 | $9.0 \times 10^9$ | 150 |
| HSV-RC/d27 | $6.5 \times 10^7$ | $9.0 \times 10^9$ | 150 | $1.2 \times 10^{10}$ | 200 |
| HSV-RC/d27 + HSV-1 | $6.5 \times 10^7$ | $1.2 \times 10^{10}$ | 200 | $3.0 \times 10^{10}$ | 500 |

5.7 Example 7 rAAVUF2 Generated by a REP-and CAP-Expressing Amplicon is Infectious

The rAAVUF2 virus prepared from the amplicon system was heat inactivated and purified on an isopycnic CsCl gradient and analyzed for its ability to transduce cells as measured by replication competence following transduction of HeLa cells.

rAAVUF2 was prepared from 6 confluent T175 flasks of UF2-293 cells ($10^8$ cells). Flasks were infected with HSV-RC/KOS (MOI of the HSV-RC/KOS was 2 recombinant genomes per cell and 2.5 pfu of wt HSV-1 per cell). After 48 h, rAAVUF2 was collected, heat inactivated for 1 h at 55° C. and CsCl gradient purified as described. The purified rAAVUF2 ($5 \times 10^5$ particles) were added to $2 \times 10^5$ HeLa cells seeded into 6 well plates 24 h earlier or the cells were mock infected. The cells were then either mock infected, infected with HSV-1 (MOI of 2.5), or infected with HSV-RC/KOS (MOI of the HSV-RC/KOS was 2 recombinant genomes per cell and 2.5 pfu of HSV-1 per cell) 24 h later. Cells were scraped 36 h later and pelleted by centrifugation (2000 rpm, 5 min). Small molecular weight DNA was isolated by Hirt extraction. Hirt extracted DNA (10 µg) was analyzed per on a 0.8% agarose gel for 12 h at 25V. DNA was transferred to a nylon membrane by Southern blotting. The membrane was probed with an [$\alpha$-$^{32}$P] dATP-labeled hgfp DNA probe, and exposed to film for 24 hours.

The replicative forms indicative of infectious rAAV were produced after the a cells transduced with rAAVUF2 were superinfected with HSV-RC/KOS. The $RF_m$ and $RF_d$ were probably not due to transduction of the cells with a recombinant HSV vector that was generated through a recombination event of the amplicon or HSV-1 helper virus with the proviral rAAVUF2. A recombinant HSV-1 vector would not be infectious after prolonged heat inactivation and purification on a CsCl gradient.

5.8 Example 8

HSV-RC/d27 Does Not Generate Wild-type AAV During the Production of rAAV

A PCR™ assay was used to detect the generation of wt AAV during production of rAAV using the HSV-1 amplicons. Primers that anneal to the D sequence and cap sequence of AAV-2 only produce a product after PCR™ amplification if wt AAV is present. An aliquot of the clarified cell lysate from GFP-92 cells infected with HSV-RC/d27 or HSV-RC/d27+wt HSV-1 (1/30th of the volume of the cell lysate, preparations one and two) was treated with DNAseI and proteinase K, phenol and chloroform extracted and precipitated in ethanol. Aliquots of the reconstituted DNA pellet (9 µl, 90% of the total volume) were then analyzed for the presence of wt AAV.

As a control, DNA template was not added to one of the PCR™ reactions. A standard curve of 1 pg, 100 fg and 10 fg of pAAV2 DNA was added to three of the PCR™ reactions. Aliquots from the PCR™ reaction using DNA from preparation (prep) 1, HSV-RC/d27; prep 1, HSV-RC/d27+HSV-1; prep 2, HSV-RC/d27 and prep 2, HSV-RC/d27+HSV-1 were analyzed. A 123 bp DNA ladder was run on the gel as a molecular weight standard. The other 1 µl from the DNA samples was analyzed for the presence of rAAVUF2 DNA using the hgfp primers to assure that DNA was present in the samples.

No product was detected in any of the preparations except the positive pAAV2 controls. A sensitivity of detection of 10 fg of pAAV2 in the PCR™ assay indicates that there is less that 1 wt AAV particle per $2 \times 10^6$ rAAV particles. In addition, the Southern blots described above were stripped and reprobed for the replicating forms of wt AAV using an [$\alpha$-$^{32}$P] dATP labeled cap DNA probe. After exposure for 7 days, no replicative intermediates of wt AAV were observed on any of the blots.

5.9 Example 9

Production of rAAV Using a Recombinant Herpes Simplex Virus Type I Vector

The vector d27.1-rc can efficiently produce rAAV from transfected 293 cells. 293 cells were transfected with AAV-GFP proviral plasmid. Approximately $3 \times 10^7$ cells were present in each experimental group. 24 h after transfection the cells were superinfected with different MOIs of d27.1-rc. 36 h post infection, a cell lysate was Recombinant adeno-associated virus type 2 vectors (rAAV) have been extremely successful vectors for in vivo gene transfer. These vectors have produced long term, high-level gene expression of therapeutic proteins in immunocompetent animal models. For example, sustained production of eryffropoietin from skelet al muscle after rAAV transductionl has been achieved in mice (Kessler et at., 1996). Therapeutic levels of Factor IX have been produced after rAAV gene transfer to the liver and skelet al muscle (Herzog et al., 1997; Koeberl et al., 1997; Nakai et al., 1998; Monahan et al., 1998). Levels of therapeutic protein production have reached up to 800 µg/ml in mice treated intramuscularly with AAV vectors expressing alpha-1 antitrypsin (Song et al., 1998). Recombinant AAV vectors have been used effectively in the central nervous system (Kaplitt et al., 1994; Peel et al., 1997; Xiao et al., 1997). In addition, rAAV has been used in human clinical trials to transfer the CFTR gene (Flotte and Carter, 1998).

Production of sufficient quantities of high-titer rAAV needed for effectiveness in vivo has been difficult to achieve, however. The process requires the efficient cellular delivery of the proviral construct to be packaged as rAAV, the AAV-2 rep and cap genes, as well as specific helper virus functions (Muzyczka, 1992). The proviral construct to be packaged contains the cDNA expression cassette flanked by AAV-2 inverted terminal repeats (ITRs). The ITRs are the cis acting viral DNA sequences required to direct replication and packaging of the rAAV vector (Samulski et al., 1983; Hermonat and Muzyczka, 1984). AAV-2 rep and cap genes encode the four Rep proteins (Rep 78, 68, 52 and 40) involved in viral DNA replication, resolution of replicative intermediates and generation of single-strand genomes and the three structural genes (VP1, VP2 and VP3) that make up the viral capsid (Berns, 1984; Chejanovsky and Carter, 1989; Samulski et al., 1987). Usually, the proviral rAAV and the rep and cap genes are introduced into cells by plasmid transfection. Replication and packaging of rAAV then occurs after expression of specific genes from a helper virus such as adenovirus (Ad) (Berns, 1984; Carter, 1990; Huang and Hearing, 1989; Samulski and Shenk, 1988; Xiao et al., 1998). Traditionally, Ad infection is used to provide helper virus functions (Muzyczka, 1992). In the case of Ad, the specific helper functions have been identified as the E1a, E1b, E2a, E4orf6 and Va RNA genes. These Ad genes encode proteins or RNA transcripts which are transcriptional regulators, and are involved in DNA replication or modify the cellular environment in order to permit efficient viral production (Berns, 1984; Carter, 1990; Huang and Hearing, 1989; Samulski and Shenk, 1988; Xiao et al., 1998).

Recent improvements in rAAV packaging technology have made production of high-titer rAAV more feasible. One significant advancement has been the development of an Ad free method for rAAV production (Xiao et al., 1998; Matsushita et al., 1998). This method is based on transfection of a plasmid encoding the Ad helper functions required for the production of rAAV. Other improvements have included the generation of rep inducible cell lines, translational control of Rep production and increasing Cap expression by driving cap transcription with a strong heterologous promoter (Clark et al., 1995; Vincent et al., 1997b; Li et al. 1997). These improved methods still possess limitations, however. The rep inducible cell lines do not produce rAAV more efficiently than traditional methods. Translational and transcriptional control of Rep and Cap production do not increase the efficiency of rAAV production more than ten fold (Vincent et al., 1997b; Li et al. 1997). The Ad free method requires successful transfection on a large scale that is not easily achieved.

While Ad is an efficient helper virus for rAAV production, little consideration has been given to other helper viruses for AAV-2 replication and packaging. Herpes simplex virus type 1 (HSV-1) is also a fully competent helper virus of AAV-2 (Rose and Koczot, 1972; Buller, 1981; Mishra and Rose, 1990; Weindler and Heilbronn, 1991). The minimal set of HSV-1 genes required for AAV-2 replication and packaging has been identified as the early genes UL5, UL8, UL52 and UL29 (Weindler and Heilbronn, 1991). These genes encode components of the HSV-1 core replication machinery—the helicase, primase and primase accessory proteins and the single-stranded-DNA binding protein (reviewed in (Knipe, 1989; Weller, 1991).

Recombinant adeno-associated virus type 2 (rAAV) vectors have recently been used to achieve long-term, high level transduction in vivo. Further development of rAAV vectors for clinical use requires significant technological improvements in large-scale vector production. In order to facilitate the production of rAAV vectors, a recombinant herpes simplex virus type I vector (rHSV-1) which does not produce ICP27, has been engineered to express the AAV-2 rep and cap genes. ICP27 is required for HSV-1 replication. Although d27.1-rc is replication defective, it does express the HSV-1 early genes required for rAAV replication and packaging (Weindler and Heilbronn, 1991; Rice and Knipe, 1990).

The vector d27.1-rc has been found to be as efficient at producing rAAV as Ad free methods and obviates the need for large-scale transfection protocols. In addition, the rHSV-1 vector is 100 times more efficient at producing rAAV than the amplicon system based on the HSV-1 helper functions described above. The optimal dose of this vector, d27.1-rc, for AAV production has been determined and results in a yield of 380 expression units (eu) of AAV-GFP produced from 293 cells following transfection with AAV-GFP plasmid DNA. In addition, d27.1-rc was also efficient at producing rAAV from cell lines that have an integrated AAV-GFP provirus. Up to 480 eu/cell of AAV-GFP could be produced from the cell line GFP-92, a proviral., 293 derived cell line. Effective amplification of rAAV vectors introduced into 293 cells by infection was also demonstrated. Passage of rAAV with d27.1-rc results in up to 200-fold amplification of AAV-GFP with each passage after coinfection of the vectors. Efficient, large-scale production (>$10^9$ cells) of AAV-GFP from a proviral cell line was also achieved and these stocks were free of replication competent AAV. The described rHSV-1 vector provides a novel, simple and flexible way to introduce the AAV-2 rep and cap genes and helper virus functions required to produce high-titer rAAV preparations from any rAAV proviral construct. The efficiency and potential for scalable delivery of d27.1-rc to producer cell cultures should facilitate the production of sufficient quantities of rAAV vectors for clinical application.

9.1 Methods 9.1.1 Plasmids

The plasmid pTR-UF5 is an AAV-GFP proviral construct with AAV-2 ITRs flanking both an eGFP and a neomycin resistance gene (neo) expression cassette. Expression of GFP is driven by the human CMV promoter. The neo gene is expressed from the HSV-1 tk promoter. The plasmid pSub201 contains the AAV-2 rep and cap genes (Samulski et al., 1987). The plasmid pHSV-106 is a pBR derived plasmid into which the BamHI fragment of HSV-1 (17+ stain) containing the thymidine kinase (tk) gene was cloned. The plasmid pHSV-106-lacZ was constructed by cloning a lacZ expression cassette into the KpnI restriction site of pHSV-106 interrupting the tk gene. The plasmid pHSV-106-rc has the AAV-2 rep and cap genes from pSub201 cloned into the KpnI site of pHSV-106.

9.1.2 Cell Lines

The 293 and Vero cell lines were obtained from American Type Culture Collection. The V27 cell line is a Vero derived cell line that expresses the HSV-1 ICP27 protein (Rice and Knipe, 1990). The C12 cell line is a HeLa derived cell line with inducible AAV-2 rep gene expression (Clark et al., 1995). The GFP-92 cell line was created by infecting 293 cells with AAV-GFP, as described herein. In AAV-GFP, expression of GFP is driven by the human CMV promoter and the neo gene is expressed from the HSV-1 tk promoter. All cell lines were maintained in Dulbecco's modified Eagle's medium (DMEM) containing 10% fetal bovine serum (FBS).

9.1.3 HSV-1 Viruses

The virus d27.1 is an ICP27 deletion mutant (Kos strain), which is propagated on the complementing cell line, V27 (Rice and Knipe 1990). The virus d27.1-rc was constructed by first creating the lacZ expressing virus d27.1-lacZ. This β-galactosidase expressing vector was created by traditional techniques involving cotransfection of d27.1 infected cell DNA and the integrating plasmid, pHSV-106-lacZ (linearized by BamHI restriction digest) into V27 cells. Recombinant viruses were isolated by screening for blue plaques after agar overlay containing 400 μg/ml halogenated indolyl-β-D-galactoside (Bluogal, Gibco-BRL). Recombinant viruses were purified by three rounds of limiting dilution. Integration was confirmed by Southern analysis of restriction enzyme digested d27.1-lacZ infected cell DNA. The virus d27.1-rc was created by cotransfection of d27.1-lacZ infected cell DNA and the SphI linearized integration plasmid pHSV-106-rc into V27 cells. Recombinant viruses were isolated by screening for white plaques after agar overlay containing 400 μg/ml Bluo-gal. Recombinant viruses were purified by three rounds of limiting dilution. Integration was confirmed by Southern analysis of restriction enzyme digested d27.1-rc infected cell DNA. The stability of integration with passage was assessed by isolating 10 clones of d27.1-rc after ten serial passages of d27.1-rc at a MOI of 0.1. All clones were able to rescue rAAV. Wild type HSV-1 virus capable of replicating on Vero cells was not detected in any preparation (limit of detection is <20 plaque forming units (PFU)/ml).

9.1.4 Recombinant AAV Production Methods

Production of AAV-GFP from pTR-UF5 transfected 293 cells. Tissue culture dishes (10 cm) plated with $2 \times 10^6$ 293 cells were transfected with 5 μg pTR-UF5 and 25 μl Lipofectamine (Gibco-BRL) as per manufacturer's instruction. Four hours post-transfection, the cells were washed and DMEM (10% FBS) was added. Twenty hours later, the cells were superinfected with d27.1-rc at different MOIs or d27.1-lacZ at a MOI of 10. (The cells on an extra transfected dish were trypsinized, resuspended and counted using a haemocytometer.) Approximately $3.5 \times 10^7$ cells were infected per MOI. Forty-eight hours later, the cells were harvested and pelleted by centrifugation (1500 rpm, 5 minutes). The cells were then resuspended in 10 ml of DMEM and cell associated rAAV was released by three rounds of freezing and thawing. Cell debris was pelleted by centrifugation (1000 rpm, 5 minutes). The cell lysates were then titered for expression units of AAV-GFP as described below and purified by CsCl gradient (Kessler et al., 1996). This experiment was repeated in triplicate.

9.1.5 Production of AAV-GFP from the Cell Line GFP-92

The GFP-92 cells were plated in 75 cm² tissue culture flasks. Twelve hours later, the cells were infected with d27.1-rc at different MOIs or d27.1-lacZ at a MOI of 10. The number of cells in one extra flask was determined as described above. Approximately $1.5 \times 10^7$ GFP-92 cells were infected per MOI. Cells were harvested 48 h post-infection and cell associated AAV-GFP was processed and titered as described above. This experiment was repeated in triplicate.

9.1.6 Production of AAV-GFP by Amplifying AAV-GFP via Infection 293 cells ($1.5 \times 10^6$ cells) were plated in six well tissue culture dishes. Twelve hours later, the cells were infected with AAV-GFP at different MOIs. Twelve hours later, the cells were infected with d27.1-rc at a MOI of 10. Cells were harvested 48 h post-infection and cell associated AAV-GFP was processed as described above. This experiment was repeated in triplicate. The amount of output rAAV was determined using the fluorescent cell assay described below.

9.1.7 Large-scale AAV-GFP Production

GFP-92 cells were plated on 175 cm² tissue culture flasks 12 h prior to infection. $1 \times 10^9$ GFP-92 cells were infected 12 h later with d27.1-rc at a MOI of 10. Cells were harvested 48 h post-infection and cell associated AAV-GFP was processed as described above. This experiment was repeated in duplicate. Stocks were analyzed for replication competent AAV (rcAAV) (Koeberl et al., 1997). Replication competent AAV was not detected (limit of detection was one replication unit per $10^7$ gfp expression units).

9.1.8 Titering of AAV-GFP in the Viral Lysates by the Fluorescent Cell Assay

Viral lysates were heat inactivated (55° C., one h). Serial dilutions of AAV-GFP were then titered on C12 cells with Ad coinfection (MOI of 20) (Clark et al., 1996). The cells were then analyzed for GFP expression using fluorescence microscopy at 48 h post-infection.

9.1.9 Western Analysis of AAV-2 Rep Proteins

The indicated cells (approximately $4 \times 10^6$ cells) were plated onto 6 cm tissue culture plates 12 h before infection with d27.1-rc (MOI as indicated). Control samples not infected. Cells were harvested 48 h post-infection and cell lysates were made and loaded on a 10% sodium dodecyl sulfate (SDS)-polyacrylamide gel followed by immunoblotting using a monoclonal antibody (clone 1F11.8, 1:5000 dilution) that recognizes all four AAV-2 Rep proteins. The antibody was detected by chemiluminescence (Amersham).

9.1.10 Immunofluorescene Assay

Cells (293, Vero or V27 cells) were plated onto a two-well tissue culture slides at a density of $1.5 \times 10^5$ cells per well. For the anti-AAV Rep immunofluorescence assay, 293 cells were infected 12 h later with d27.1-rc at a MOI of 10. Cells were washed with DMEM after a 45 minute adsorption period and DMEM with 10% FBS was then added. After 10 h, cells were washed twice with PBS and fixed for 10 minutes in 4% paraformaldehyde in PBS. Cells were washed twice with PBS and permeabilized with 0.2% Triton X-100 in PBS for two minutes. Cells were then washed twice with PBS and incubated for one hour at 37° C. in a humidified chamber with monoclonal anti-Rep antibody (American Research Products, clone 226.7, 1:1 dilution). This antibody recognizes all four Rep proteins. The cells were then washed three times with PBS and incubated for 30 minutes at 37° C. with FITC conjugated, donkey-anti-mouse secondary antibody (diluted 1:100 in 2% goat serum, 2% donkey serum in PBS). The slides were then washed three times, covered with a 4',6-diamidino-2-phenylindole (DAPI) containing mounting solution Vector Laboratories), sealed and analyzed for immunofluorescence. Microscopy was performed on a Leitz microscope with Image Pro acquisition equipment and image analysis software.

To analyze the maturation of HSV-1 viral replication centers and Rep expression in V27 cells after d27.1-rc infection, a rabbit polyclonal anti-ICP8 (the HSV-1 single-stranded-DNA binding protein) antibody (PAb 3-83) and the monoclonal anti-Rep antibody (American Research Products, clone 226.7, 1:1 dilution) were utilized in a double label experiment. All procedures were as previously described except that V27 cells were infected at a MOI of one. After fixing and permeablization, V27 cells were incubated as above with the anti-Rep monoclonal antibody. The cells were then washed twice with PBS and incubated with the anti-ICP8 antibody (diluted 1:50 in 2% goat serum, 2% donkey serum in PBS) for one hour in a humidified chamber at 37° C. The cells were then washed three times with PBS and then incubated with a rhodamine conjugated, donkey-anti-rabbit secondary antibody and FITC conjugated, donkey-anti-mouse secondary antibody (both diluted 1:100 in 2% goat serum, 2% donkey serum in PBS) for 30 minutes at 37° C. The slides were then washed three times, covered with DAPI containing mounting solution, sealed and analyzed for immunofluorescence. Vero cells were infected and processed along side V27 cells to serve as positive controls for Rep staining.

9.2 Results 9.2.1 Construction and Characterization of d27.1-RC

The rHSV-1, d27.1-rc was constructed by homologous recombination of the AAV-2 rep and cap genes into the tk locus of the rHSV-1 virus d27.1 (FIG. 2). In this recombinant virus, the AAV-2 rep and cap genes are under control of their native promoters- the p5, p19 and p40 promoters. The p5, p19 and p40 promoters drive expression of the AAV-2 proteins Rep 78 and 68, Rep 52 and 40, and the capsid structural proteins VP1, VP2 and VP3, respectively (Carter et al., 1983; Green and Roeder, 1980; Laughlin et al., 1979; Lusby et al., 1980; Marcus et al., 1981). Homologous recombination into the tk gene was confirmed by Southern blot analysis of restriction digests of d27.1-rc infected cell DNA. In addition, d27.1-rc plaque formation on V27 cells, a complementing cell line, was not affected by 5-bromo-deoxycytidine. This indicates that the tk gene, appropriately, did not produce functional thymidine kinase.

9.2.2 Production of AAV-2 Rep by d27.1-rc

In order for d27.1-rc to replicate rAAV, the AAV-2 Rep proteins must be efficiently expressed and localized to the nucleus of the cell after d27.1-rc infection. To determine the level of expression of the AAV-2 Rep proteins from d27.1-rc, Western analysis was utilized. The expression of the AAV-2 Rep proteins from d27.1-rc after infection of three different cell lines (293, Vero and V27 cells) at different multiplicities of infection (MOI; 0, 0.1, 1 and 5 infectious units/cell) was analyzed.

The vector d27.1-rc expressed different levels of each of the AAV-2 Rep proteins in the different cell lines. In 293 cells, high level expression of all four Rep proteins occurred after infection with d27.1-rc. Expression of the Rep proteins was also observed in Vero cells after d27.1-rc infection. In contrast, only a small amount of Rep was produced in V27 cells after d27.1-rc infection, especially at higher MOIs. The level of Rep expression after d27.1-rc infection of 293 and Vero cells was observed to be dependent on the MOI. The higher level expression of Rep in 293 cells after d27.1-rc infection may be due to upregulation of the p5 promoter by Ad E1a present in 293 cells. The low level of Rep expressed in V27 cells after d27.1-rc infection in part results from lytic replication of d27.1-rc after infection of this cell line.

9.2.3 The Rep Produced by d27.1-rc Localizes to the Nucleus

The cellular distribution of the AAV-2 Rep proteins was determined in an immunofluorescence assay (IFA) which utilized a monoclonal antibody that recognizes the four Rep proteins. The IFA was conducted 10 h after infection of 293 cells with d27.1-rc. The 293 cells were processed for IFA and the cells were incubated with a monoclonal antibody that detects all four Rep proteins (78, 68, 52, and 40). The cells were then incubated with a FITC conjugated, donkey-anti-mouse secondary antibody.

The Rep proteins, expressed after infection of 293 cells by d27.1-rc, localized to discrete nuclear punctate bodies. The distribution of Rep proteins to the nucleus of 293 cells infected with d27.1-rc is a prerequisite for rAAV replication.

9.2.4 Replication Center Formation by d27.1-rc

The observation has been made that the rep gene products are capable of inhibiting viral and cellular DNA replication (Khleif et al., 1991; Heilbronn et al., 1990; Weitzman et al., 1996a). In particular, rep gene products have been shown to be potent inhibitors of Ad DNA replication and prevent the maturation of Ad DNA replication centers (Weitznan et al., 1996b). This inhibitory effect of Rep proteins is presumably responsible for the inability to generate a recombinant Ad that expresses the AAV-2 rep gene. If rep gene products similarly inhibited HSV-1 viral DNA replication, the recombinant virus, d27.1-rc, would not be able to propagate. Replication of d27.1-rc was not affected by the presence of the rep gene, however. The kinetics of plaque formation on V27 cells, the complementing cell line, and the amount of virus produced per cell was identical to the parent virus, d27.1.

In addition, the development of HSV-1 DNA replication centers after d27.1-rc infection of V27 cells was not affected by the presence of the rep gene. HSV-1 replication centers develop in the nuclei of infected cells in a time dependent manner (Quinlan et al., 1984). Viral and cellular proteins required for viral DNA replication (such as the HSV-1 core replication proteins which includes ICP8, the single-stranded-DNA binding protein) and replicating viral DNA localize to these centers (Quinlan et al., 1984; Liptak et al., 1996; Lukonis and Weller, 1996; Zhong and Hayward, 1997).

The immunofluorescence assay showing the development of mature HSV-1 viral DNA replication centers and minimal Rep expression in V27 cells after infection with d27.1-rc was conducted as follows. Twelve hours after infection (MOI of 1), V27 cells were processed for IFA and incubated with a rabbit, anti-ICP8 antibody and a monoclonal, anti-Rep antibody. The cells were then incubated with a rhodamine conjugated, donkey-anti-rabbit secondary antibody and a FITC conjugated, donkey-anti-mouse secondary antibody.

Mature HSV-1 replication centers were observed in the nuclei of V27 cells 12 h after d27.1-rc infection, as indicated by the distribution of ICP8. This distribution of ICP8 is characteristic of fully developed HSV-1 replication centers (Zhong and Hayward, 1997) and did not differ from replication centers formed in V27 cells by the parent virus, d27.1. In addition, minimal AAV-2 Rep expression was observed in V27 cells after d27.1-rc infection.

9.2.5 The Vector d27.1-rc is Efficient at Producing Infectious rAAV from Different rAAV Proviral Templates To determine the flexibility and efficiency of rAAV production using d27.1-rc, the production of rAAV from proviral plasmid transfected into cells, from a proviral cell line and by amplifying rAAV by coinfection was studied. The vector d27.1-rc was observed to effectively rescue rAAV from pTR-UF5 transfected 293 cells. The plasmid pTR-UF5 contains a proviral rAAV genome that encodes the green fluorescent protein (GFP) (Zolotukhin et al., 1996).

The purified AAV-GFP produced by d27.1-rc was shown to be infectious. C12 cells were infected with the AAV-GFP (MOI of 5 eu) produced by d27.1-rc. The cells were then coinfected with Ad (MOI of 20). Fluorescent microscopy was used to detect GFP expression 24 h after infection. Transfection of 293 cells with pTR-UF5 followed by superinfection with d27.1-rc resulted in rescue of infectious AAV-GFP (FIG. 3). The amount of AAV-GFP produced was a function of the MOI of d27.1-rc. An increase in the yield of AAV-GFP was observed up to an MOI of 10. At this MOI, the yield of AAV-GFP was 381 eu/cell. This level of production compares favorably with recently developed rAAV production protocols based upon Ad free transfection procedures (Xiao et al., 1998; Matsushita et al., 1998). Infection of pTR-UF5 transfected 293 cells with a control virus, d27.1-lacZ, at an MOI of 10 did not produce AAV-GFP.

The vector d27.1-rc was also capable of efficient AAV-GFP production from the cell line GFP-92 (FIG. 4). In the cell line GFP-92, a proviral rAAV genome that encodes GFP is integrated into the chromosomal DNA. As in the transfection experiment, the amount of AAV-GFP produced was observed to be a function of the MOI of d27.1-rc. At the most efficient MOI for AAV-GFP replication and packaging, 480 eu/cell was produced using the vector d27.1-rc. Infection of this cell line with the control virus d27.1-lacZ at an MOI of 10 did not produce AAV-GFP.

9.2.6 Amplification of rAAV via Co-infection with rHSV

Interestingly, d27.1-rc can also be used to amplify rAAV genomes introduced into cells by infection of rAAV (Table 3). 293 cells were infected with different MOIs of AAV-GFP as indicated. 12 h after infection, the cells were superinfected with d27.1-rc a t a MOI of 10. 48 h post-infection a cell lysate was made from the infected cells by three rounds of freeze-thaw. The viral lysate was heat inactivated at 55° C. for one hour and then titered in duplicate on C12 cells that were coinfected with adenovirus (MOI of 20). 48 h post-infection the C12 cells were analyzed for GFP expression using fluorescent microscopy and a titer was determined (expression units). The data represents duplicate experiments.

TABLE 3

SERIAL PASSAGE OF RAAV WITH
D27.1-RC RESULTS IN VECTOR AMPLIFICATION

| Passage Number | Input Vector | Output Vector | Fold Amplification | Total Amplification |
|---|---|---|---|---|
| 1 | $5.0 \times 10^3$ | $1.0 \times 10^6$ | 200 | 200 |
| 2 | $1.0 \times 10^4$ | $1.75 \times 10^6$ | 175 | $3.5 \times 10^4$ |
| 3 | $1.75 \times 10^4$ | $2.97 \times 10^7$ | 170 | $5.95 \times 10^6$ |

When rAAV and rHSV are co-infected in 293 cells amplification of rAAV genomes observed. Infection with d27.1-rc (MOI of 10) along with rAAV (MOI of 0.01) leads to a 200 fold amplification of input AAV-GFP. The total amplification of rAAV was greater than $10^6$ after three cycles of passage. While not as efficient as the production of AAV-GFP from transfected plasmid or a proviral cell line, coinfection of rAAV vectors with d27.1-rc permits serial amplification of rAAV via scalable infection.

9.2.7 The Efficiency of rAAV Production by d27.1-rc is Maintained when the Scale of Production is Increased To verify that d27.1-rc can be utilized to produce rAAV on a larger scale, $10^9$ GFP-92 cells were infected with d27.1-rc (Table 4).

TABLE 4

EFFICIENT LARGE-SCALE PRODUCTION OF
RAAV IS OBSERVED USING D27.1-RC

| Study Number | Number of GFP-92 cells | Amount of virus produced in cell lysate (eu) | Expression units produced per cell |
|---|---|---|---|
| 1 | $1.0 \times 10^9$ | $3.8 \times 10^{11}$ | 380 |
| 2 | $1.1 \times 10^9$ | $3.7 \times 10^{11}$ | 338 |

The yield of AAV-GFP, 380 eu/cell and 338 eu/cell in duplicate experiments, indicates that d27.1-rc is able to efficiently produce rAAV after the scale of infection is increased. Maintaining efficient rAAV production as the scale of d27.1-rc infection is increased is required for d27.1-rc to be a viable method for large-scale production of rAAV.

9.3 Recombinant HSV Vector Expressing AAV Rep and Cap Results in High-titer rAAV Production Recombinant adeno-associated virus mediated gene transfer has been uniquely successful in achieving long-term, high-level gene expression in vivo. Many potential applications for the use of rAAV in genetic disease require a substantial vector dose to achieve a therapeutic effect. One significant problem associated with rAAV vectors, has been the difficulty in generating sufficient quantities of high-titer vector required for in vivo applications. This difficulty has led to improvements in numerous aspects of rAAV vector development in order to increase the efficiency of rAAV production. These strategies have all involved the use of adenovirus to provide the helper functions for rAAV production, however. Few studies have explored the possibility of using other helper viruses of AAV-2 replication and packaging for large-scale production.

This Example describes the development of an alternative system for production of rAAV. This system is based upon the HSV-1 helper functions of AAV-2 replication and packaging. By generating a recombinant HSV-1 encoding the AAV-2 rep and cap genes, a single infectious helper has been created. The expression of Rep from this vector appears to be regulated and is appropriately distributed to the nucleus. The rHSV-1, d27.1-rc, propagates readily and its replication is not affected by the presence of rep.

Development of mature HSV-1 replication centers in the presence of rep appears to be unique to this vector. One possible explanation why the presence of the rep gene did not affect the kinetics of d27.1-rc replication or the formation of mature viral replication centers is that Rep proteins are not efficiently expressed in the V27 cells after d27.1-rc infection. Both Western analysis and an IFA were used to analyze Rep expression in 293, Vero and V27 cells after d27.1-rc infection. By Western analysis, high level Rep expression was observed in 293 cells and Vero cells but not in V27 cells after infection with d27.1-rc. By IFA, Rep expression was observed in the nucleus of infected 293 cells and Vero cells after infection with d27.1-rc, but not in V27 cells. The minimal Rep expression after d27.1-rc infection of V27 cells may explain how generation of d27.1-rc was feasible and why similar efforts to construct recombinant Ad vectors with the rep gene have failed.

The d27.1 vector was chosen as the mutant background to provide the viral helper functions for several reasons. The vector d27.1 has a mutation in the immediate early gene IE63 and does not produce ICP27 (Rice and Knipe, 1990). The protein ICP27 has been implicated in the inhibition of host cell mRNA splicing (Sandri-Goldin and Mendoza, 1992; McLauchlan et al., 1992). The use of d27.1 minimizes inhibition of splicing of the rep and cap messages compared to a vector which produces ICP27. In addition, d27.1 overexpresses ICP8 (Rice and Knipe, 1990), one of the HSV-1 genes essential for AAV-2 replication (Weindler and Heilbronn, 1991). High level expression of ICP8, the single-stranded DNA binding protein, is beneficial for rAAV production.

The most efficient manner in which d27.1-rc is used for large scale rAAV production involves infection of a proviral cell line that provides the rAAV template to be packaged. In this two-part system, the proviral cell line is grown at high densities in large quantities in spinner cultures or cartridge systems. The AAV-2 rep and cap genes and the helper functions required for rAAV production are then provided by d27.1-rc infection. Using d27.1-rc to infect the proviral cells eliminates the need for transfection at any step in the production process. The choice of cell line used for this system is important, however. The results of Western analysis indicate that d27.1-rc efficiently expresses the AAV-2 Rep proteins only in certain cell lines.

The dose response curve for the production of AAV-GFP by d27.1-rc demonstrates that increasing the MOI of d27.1-rc augments rAAV production to a point. The vector d27.1- rc still expresses the immediate early genes that encode the viral proteins ICP0 and ICP4 (Rice and Knipe, 1990). Expression of these immediate early genes is detrimental to the cell and induces cell death (Johnson et al., 1992b; Johnson and Curtis, 1994). At high MOIs, increased expression of these immediate early genes probably leads to rapid cell death, limiting the production of rAAV. At a MOI of 25, while there is increased expression of the AAV-2 rep genes and the HSV-1 helper genes necessary for rAAV production, increased cytotoxicity due to additional gene expression from the vector also occurs. At a MOI of 10, the most effective balance exists between expression of the AAV-2 rep and cap genes and HSV-1 helper functions required for rAAV production and the cytotoxicity inherent to the vector.

Replication of HSV-1 is not required for efficient replication and packaging of AAV-2 (Weindler and Heilbronn, 1991). Cells lines such as 293 cells, which do not complement d27.1-rc replication, can therefore be used to produce rAAV. Using a non-complementing cell line to produce rAAV permits the production of rAAV without generating additional d27.1-rc. The helper virus, d27.1-rc, is therefore effectively eliminated from the rAAV produced.

The application of a recombinant virus to introduce the AAV-2 rep and cap and helper virus functions into cells in order to produce rAAV has certain advantages over the amplicon system described above. Unlike a recombinant HSV-1 vector, an amplicon system has a variable helper virus to amplicon virus ratio from passage to passage. This variability makes optimization of an amplicon system for rAAV production difficult since the ratio of helper virus to amplicon virus effects the amount of rAAV produced. In addition, there is no selective pressure to maintain the recombinant AAV-2 genome in the amplicon. With passage, deletion and recombination of the amplicon genome is likely to occur, resulting in decreased efficiency of rAAV production after serial passage of the amplicon. These problems are not encountered using the recombinant virus d27.1-rc.

Large-scale production of rAAV vectors is required for in vivo preclinical and clinical trials of potentially therapeutic rAAV vectors. The vector d27.1-rc facilitates the production of rAAV. The vector d27.1-rc is flexible and can be utilized to produce rAAV from transfected cells, cell lines or even infected rAAV. The rescue of rAAV from proviral cell lines at or above the efficiency of Ad free methods permits large-scale production of rAAV without requiring a transfection procedure. Combined with recently developed purification procedures (Xiao et al., 1998, Grimm et al., 1998, Zolotukhin et al., 1999), d27.1-rc is an attractive way to produce the large quantity of rAAV that is needed for clinical success of rAAV based gene therapy.

6.0 REFERENCES

The following references, to the extent that they provide exemplary procedural or other details supplementary to those set forth herein, are specifically incorporated herein by reference.

U.S. Pat. No. 4,237,224, issued Dec. 2, 1980.
U.S. Pat. No. 4,554,101, issued Nov. 19, 1985.
U.S. Pat. No. 4,683,195, issued Jul. 28, 1987.
U.S. Pat. No. 4,683,202, issued Jul. 28, 1987.
U.S. Pat. No. 4,800,159, issued Jan. 24, 1989.
U.S. Pat. No. 4,883,750, issued Nov. 28, 1989.
U.S. Pat. No. 5,145,684, issued Sep. 8, 1992.
U.S. Pat. No. 5,279,721, issued Jan. 18, 1994.
U.S. Pat. No. 5,455,166, issued Oct. 3, 1995.
U.S. Pat. No. 5,501,971, issued Mar. 26, 1996.
U.S. Pat. No. 5,552,157, issued Sep. 3, 1996.
U.S. Pat. No. 5,565,213, issued Oct. 15, 1996.
U.S. Pat. No. 5,567,434, issued Oct. 22, 1996.
U.S. Pat. No. 5,648,211, issued Jul. 15, 1997.
U.S. Pat. No. 5,712,124, issued Jan. 27, 1998.
U.S. Pat. No. 5,744,311, issued Apr. 28, 1998.
U.S. Pat. No. 5,661,033, issued Aug. 26, 1997.
U.S. Pat. No. 5,738,868, issued Apr. 14, 1998.
U.S. Pat. No. 5,741,516, issued Apr. 21, 1998.
U.S. Pat. No. 5,795,587, issued Aug. 18, 1998.
U.S. Pat. No. 5,879,934, issued Mar. 9, 1999.
Eur. Pat. Appl. Publ. No. 320,308.
Eur. Pat. Appl. Publ. No. 329,822.
Great Britain Pat. Appl. No. 2202328.
Intl. Pat. Appl. Publ. No. WO 88/10315.
Intl. Pat. Appl. Publ. No. WO 89/06700.
Intl. Pat. Appl. Publ. No. WO 90/07641.
Intl. Pat. Appl. No. PCT/US87/00880.
Intl. Pat. Appl. No. PCT/US89/01025.
Afione et at, "In vivo model of adeno-associated virus vector persistence and rescue," *J. Virol.* 70:3235–3241, 1996.
Allen and Choun, "Large unilamellar liposomes with low uptake into the reticuloendothelial system," *FEBS Lett.* 223:42–46, 1987.
Atchinson et al., *Science* 194:754–756, 1965.
Balazsovits et al., "Analysis of the effect of liposome encapsulation on the vesicant properties, acute and cardiac toxicities, and antitumor efficacy of doxorubicin," *Cancer Chemother. Pharmacol.* 23:81–86, 1989.
Berns et al., "Regulation of adeno-associated virus DNA replication," *Biochim. Biophys. Acta* 951:425–429, 1988.
Berns, In: *The parvoviruses*, Plenum Press, New York, 1984.
Berns et al., In: *Virus Persistence*, Mehay et al. (Ed.), Cambridge Univ. Press, pp. 249–265, 1982.
Berns et al., "Detection of adeno-associated virus (AAV)-specific nucleotide sequences in DNA isolated from latently infected Detroit 6 cells," *Virology* 68:556–560, 1975.
Breakefield et al., *Treatment of Genetic Diseases*, Churchill Livingstone, Inc., 1991.
Buller, "Herpes simplex virus types 1 and 2 completely help adenovirus-associated virus replication," *J. Virol.* 40:241–247, 1981.
Capecchi, "High efficiency transformation by direct microinjection of DNA into cultured mammalian cells," *Cell* 22:479–488, 1980.
Carter et al., "Properties of an adenovirus type 2 mutant, Ad2d1807, having a deletion near the right-hand genome terminus: failure to help AAV replication," *Virology* 126:505–516, 1983.
Carter, "The growth of adeno-associated virus," (P. Tijssen, ed.), In: *Handbook of Parvoviruses*, CRC Press, Boca Raton, pp. 155–168, 1990.
Challberg, "A method for identifying the viral genes required for herpesvirus DNA replication," *Proc. Natl. Acad. Sci. USA* 83:9094–9103, 1986.
Chejanovsky and Carter, "Mutagenesis of an AUG codon in the adeno-associated virus rep gene: effects on viral DNA replication," *Virolosy* 173:120–128, 1989.
Chen and Okayama, "High-efficiency transformation of mammalian cells by plasmid DNA," *Mol. Cell. Biol.* 7:2745–2752, 1987.
Cheung et al., "Integration of the adeno-associated virus genome into cellular DNA in latently infected human Detroit 6 cells," *J. Virol.* 33:739–748, 1980.
Chiorini et al., "High-efficiency transfer of the T cell co-stimulatory molecule B7-2 to lymphoid cells using high-titer recombinant adeno-associated virus vectors," *Hum. Gene Ther.* 6:1531–1541, 1995.

Chocca et al., *The New Biologist* 2:739–746, 1990.

Clark et al., "A stable cell line carrying adenovirus-inducible rep and cap genes allows for infectivity titration of adeno-associated virus vectors," *Gene Therapy* 3:1124–1132, 1996.

Clark et al., "Cell lines for the production of recombinant adeno-associated virus," *Hum. Gene Ther.* 6:1329–1341, 1995.

Clark et al., "Highly purified recombinant adeno-associated virus vectors are biologically active and free of detectable helper and wild-type viruses," *Hum. Gene Ther.* 10:1031–1039, 1999.

Clark et al., "Recombinant adeno-associated viral vectors mediate long-term transgene expression in muscle," *Hum. Gene Ther.* 8:659–669, 1997.

Coune, "Liposomes as drug delivery system in the treatment of infectious diseases: potential applications and clinical experience," *Infection* 16:141–147, 1988.

Couvreur et al., "Nanocapsules, a new lysosomotropic carrier," *FEBS Lett.* 84:323–326, 1977.

Couvreur et al., "Tissue distribution of antitumor drugs associated with polyalkylcyanoacrylate nanoparticles," *J. Pharm. Sci.* 69:199–202, 1980.

Couvreur, "Polyalkyleyanoacrylates as colloidal drug cariers," *Crit. Rev. Ther. Drug Carrier Syst.* 5:1–20, 1988.

Crute et al., "Herpes simplex virus 1 helicase-primase: a complex of three herpes-encoded gene products," *Proc. Natl. Acad. Sci. USA* 86:2186–2194, 1989.

Cukor et al., In: *The Paroviruses*, K. I. Berns (Ed.), Plenum, NY, pp. 33–66, 1984.

Curiel et al., "Adenovirus enhancement of transferrin-polylysine-mediated gene delivery," *Proc. Natl. Acad. Sci. USA* 88:8850–8854, 1991.

DeLuca et al., "Isolation and characterization of deletion mutants of herpes simplex virus type 1 in the gene encoding immediate-early regulatory protein ICP4," *J. Virol.* 56:558–570, 1985.

DeLuca et al., "Activities of herpes simplex virus type 1 (HSV-1) ICP4 genes specifying nonsense peptides," *Nucleic Acids Res.* 15:4491–511, 1987.

DeLuca et al., "Physical and functional domains of the herpes simplex virus transcriptional regulatory protein ICP4," *J. Virol.* 62:732–43, 1988.

Douglas et al., "Nanoparticles in drug delivery," *Crit. Rev. Ther. Drug Carrier Syst.* 3:233–261, 1987.

Faller and Baltimore, "Liposome encapsulation of retrovirus allows efficient super infection of resistant cell lines," *J. Virol.* 49:269–272, 1984.

Fechheimer et al., "Transfection of mammalian cells with plasmid DNA by scrape loading and sonication loading," *Proc. Natl. Acad. Sci. USA* 84:8463–8467, 1987.

Fisher et al., "Recombinant adeno-associated virus for muscle directed gene therapy," *Nat. Med.* 3:306–312, 1997.

Flannery, "Efficient photoreceptor-targeted gene expression in vivo by recombinant adeno-associated virus," *Proc. Natl. Acad Sci. USA* 94:6916–6921, 1997.

Flotte and Carter, "Adeno-associated virus vectors for gene therapy of cystic fibrosis," *Methods Enzymol.* 292:717–73, 1998.

Flotte et al., "An improved system for packaging recombinant adeno-associated virus vectors capable of in vivo transduction," *Gene Ther.* 2:29–37, 1995.

Flotte et al., "Stable in vivo expression of the cystic fibrosis transmembrane conductance regulator with an adeno-associated virus vector," *Proc. Natl. Acad. Sci. USA* 90:10613–10617, 1993.

Flotte et al., "A phase I study of an adeno-associated virus-CFTR gene vector in adult CF patients with mild lung disease," *Hum. Gene Ther.* 7:1145–1159, 1996.

Fraley et at., "Entrapment of a bacterial plasmid in phospholipid vesicles: Potential for gene transfer," *Proc. Natl. Acad. Sci. USA* 76:3348–3352, 1979.

Fresta and Puglisi, "Application of liposomes as potential cutaneous drug delivery systems. In vitro and in vivo investigation with radioactively labeled vesicles," *J. Drug Target* 4:95–101, 1996.

Frohman, In: "PCR Protocols: A Guide To Methods And Applications", Academic Press, N.Y., 1990.

Fromm et al., "Expression of genes transferred into monocot and dicot plant cells by electroporation," *Proc. Natl. Acad. Sci. USA* 82:5824–5828, 1985.

Gabizon and Papahadjopoulos, "Liposomes formulations with prolonged circulation time in blood and enhanced uptake by tumors," *Proc. Natl. Acad Sci. USA* 85:6949–6953, 1988.

Gopal, "Gene transfer method for transient gene expression, stable transfection, and cotransfection of suspension cell cultures," *Mol. Cell Biol.* 5:1188–1190, 1985.

Graham and van der Eb, "Transformation of rat cells by DNA of human adenovirus 5," *Virology* 54:536–539, 1973.

Green and Roeder, "Transcripts of the adeno-associated virus genome: mapping of the major RNAs," *J. Virol.* 36:79–92, 1980.

Grimm et al., "Novel tools for production and purification of recombinant adenoassociated virus vectors," *Hum. Gene Ther.* 9:2745–2760, 1998.

Handa et al., "Establishment and characterization of KB cell lines latently infected with adeno-associated virus type 1," *Virology* 82:84–92, 1977.

Harland and Weintraub, "Translation of mammalian mRNA injected into Xenopus oocytes is specifically inhibited by antisense RNA," *J. Cell Biol.* 101:1094–1099, 1985.

Heath and Martin, "The development and application of protein-liposome conjugation techniques," *Chem. Phys. Lipids*, 40:347–358, 1986.

Heath et al., "Liposome-mediated delivery of pteridine antifolates to cells: in vitro potency of methotrexate and its alpha and gamma substituents," *Biochim. Biophys. Acta*, 862:72–80, 1986.

Heilbronn et al., "The adeno-associated virus rep gene suppresses herpes simplex virus-induced DNA amplification," *J. Virol.* 64:3012–3018, 1990.

Henry-Michelland et al., "Attachment of antibiotics to nanoparticles; Preparation, drug-release and antimicrobial activity in vitro," *Int. J. Pharm.* 35:121–127, 1987.

Hermonat and Muzyczka, "Use of adeno-associated virus as a mammalian DNA cloning vector: transduction of neomycin resistance into mammalian tissue culture cells," *Proc. Natl. Acad Sci. USA* 81:6466–6470, 1984.

Herzog et al., "Stable gene transfer and expression of human blood coagulation factor IX after intramuscular injection of recombinant adeno-associated virus," *Proc. Natl. Acad. Sci. USA* 94:5804–5809, 1997.

Hirt, "Selective extraction of polyoma DNA from infected mouse cell cultures," *Mol. Cell Biol.* 26:365–369, 1967.

Hoggan et al., In: *Proceeding of the Fourth Lepetit Colloquium*, Cacoyac, Mexico, North Holland, Amsterdam, pp. 243–249, 1972.

Hoggan, *Fed. Proc.* 24:248, 1965.

Huang and Hearing, "Adenovirus early region 4 encodes two gene products with redundant effects in lytic infection," *J. Virol.* 63:2605–2615, 1989.

Im and Muzyczka, "The AAV origin binding protein Rep68 is an ATP-dependent site-specific endonuclease with DNA helicase activity, *Cell* 61:447–457, 1990.

Imaizumni et al., "Liposome-entrapped superoxide dismutase reduces cerebral infarction in cerebral ischemia in rats," *Stroke* 21:1312–1317, 1990a.

Imaizumi et al., "Liposome-entrapped superoxide dismutase ameliorates infarct volume in focal cerebral ischemia," *Acta. Neurochirurgica Suppl.* 51:236–238, 1990b.

Inoue and Russell, "Packaging cells based on inducible gene amplification for the production of adeno-associated virus vectors," *J Virol.* 72:7024–7031, 1998.

Johnson and Curtis, "Preventive therapy for periodontal diseases," *Adv. Dent. Res.* 8:337–348, 1994.

Johnson et al., "Cytotoxicity of a replication-defective mutant of herpes simplex virus type 1," *J. Virol.* 66:2952–2965, 1992a.

Johnson et al., "Efficiency of gene transfer for restoration of normal airway epithelial function in cystic fibrosis," *Nat. Genet.* 2:21–25, 1992b.

Johnson et al., "Improved cell survival by the reduction of immediate-early gene expression in the replication-defective mutants of herpes simplex virus type 1 but not by mutation of the virion host shutoff function," *J. Virol.* 68:6347–6362, 1994.

Johnston et al., "HSV/AAV hybrid amplicon vectors extend transgene expression in human glioma cells," *Hum. Gene Ther.* 8:359–370, 1997.

Jooss et al., "Transduction of dendritic cells by DNA viral vectors directs the immune response to transgene products in muscle fibers," *J. Virol.* 727:4212–4223, 1998.

Kaplitt et al., "Long-term gene expression and phenotypic correction using adeno-associated virus vectors in the mammalian brain," *Nat. Genet.* 8:148–154, 1994.

Kessler et al., "Gene delivery to skelet al muscle results in sustained expression and systemic delivery of a therapeutic protein, *Proc. Natl. Acad Sci. USA* 93:14082–14087, 1996.

Khleif et al., "Inhibition of cellular transformation by the adeno-associated virus rep gene," *Virology* 181:738–741, 1991.

Klein et al., "High-velocity microprojectiles for delivering nucleic acids into living cells. 1987," *Biotechnology* 24:384–386, 1992.

Klein, "Neuron-specific transduction in the rat septohippocampal or nigrostriatal pathway by recombinant adeno-associated virus vectors," *Exper. Neurol.* 150:183–194, 1998.

Knipe et al., "Characterization of two conformational forms of the major DNA-binding protein encoded by herpes simplex virus 1," *J. Virol.* 44:736–741, 1982.

Knipe, "The role of viral and cellular nuclear proteins in herpes simplex virus replication," *Adv. Virus Res.* 37:85–123, 1989.

Koeberl et al., "Persistent expression of human clotting factor IX from mouse liver after intravenous injection of adeno-associated virus vectors," *Proc. Natl. Acad Sci. USA* 94:1426–1431, 1997.

Kotin and Berns, "Organization of adeno-associated virus DNA in latently infected Detroit 6 cells," *Virology* 170:460–467, 1989.

Kotin et al., "Characterization of a preferred site on human chromosome 19q for integration of adeno-associated virus DNA by non-homologous recombination," *EMBO J.* 11:5071–5078, 1992.

Kotin et al., "Site-specific integration by adeno-associated virus," *Proc. Natl. Acad. Sci. USA* 87:2211–2215, 1990.

Kotin, "Prospects for the use of adeno-associated virus as a vector for human gene therapy," *Hum. Gene Ther.* 5:793–801, 1994.

Kuby, In: *Immunology*, 2nd Edition, W.H. Freeman & Company, New York, 1994.

Kyte and Doolittle, "A simple method for displaying the hydropathic character of a protein," *J. Mol. Biol.* 157:105–132, 1982.

Lasic, "Novel applications of liposomes," *Trends Biotechnol.* 16:307–321, 1998.

Laughlin et al., "Defective-interfering particles of the human parvovirus adeno-associated virus," *Virology* 94:162–174, 1979.

Laughlin et al., "Cloning of infectious adeno-associated virus genomes in bacterial plasmids," *Gene* 23:65–73, 1983.

Lewin et al., "Ribozyme rescue of photoreceptor cells in a transgenic rat model of autosomal dominant retinitis pigmentosa," *Nat. Med.* 4:967–971, 1998.

Li et al., "Role for highly regulated rep gene expression in adeno-associated virus vector production," *J. Virol.* 71:5236–5243, 1997.

Liptak et al., "Functional order of assembly of herpes simplex virus DNA replication proteins into prereplicative site structures," *J. Virol.* 70:1759–1767, 1996.

Lopez-Berestein et al., "Liposomal amphotericin B for the treatment of systemic fangal infections in patients with cancer: a preliminary study" *J. Infect. Dis.* 2151:704, 1985a.

Lopez-Berestein et al., "Protective effect of liposomal-amphotericin B against *C. albicans* infection in mice," *Cancer Drug Delivery* 2:183, 1985b.

Lukonis and Weller, "Characterization of nuclear structures in cells infected with herpes simplex virus type 1 in the absence of viral DNA replication," *J. Virol.* 70:1751–1758, 1996.

Lusby et al., "Nucleotide sequence of the inverted terminal repetition in adeno-associated virus DNA," *J. Virol.* 34:402–409, 1980.

Lusby and Berns, "Mapping of the 5' termini of two adeno-associated virus 2 RNAs in the left half of the genome," *J. Virol.* 41:518–526, 1982.

Maloy et al., In: *Microbial Genetics*, 2nd Edition, Jones and Barlett Publishers, Boston, Mass., 1994.

Maniatis et al., "Molecular Cloning: a Laboratory Manual," Cold Spring Harbor Laboratory, Cold Spring Harbor, N.Y., 1982.

Marcus et al., "Adeno-associated virus RNA transcription in vivo," *Eur. J. Biochem.* 121:147–154, 1981.

Matsushita et al., "Adeno-associated virus vectors can be efficiently produced without helper virus," *Gene Ther.* 5:938–945, 1998.

McCarthy et al., "Herpes simplex virus type 1 ICP27 deletion mutants exhibit altered patterns of transcription and are DNA deficient," *J. Virol.* 63:18–27, 1989.

McLauchlan et al., "Herpes simplex virus IE63 acts at the posttranscriptional level to stimulate viral mRNA 3' processing," *J. Virol.* 66:6939–6945, 1992.

Mishra and Rose, "Adeno-associated virus DNA replication is induced by genes that are essential for HSV-1 DNA synthesis," *Virology* 179:632–639, 1990.

Monahan et al., "Direct intramuscular injection with recombinant AAV vectors results in sustained expression in a dog model of hemophilia," *Gene Ther.* 5:40–49, 1998.

Mori and Fukatsu, "Anticonvulsant effect of DN-1417 a derivative of thyrotropin-releasing hormone and liposome-entrapped DN-1417 on amygdaloid-kindled rats," *Epilepsia* 33:994–1000, 1992.

Muller et al., "Efficient transfection and expression of heterologous genes in PC12 cells," *Cell, Biol.* 9:221–229, 1990.

Muzyczka, "Use of adeno-associated virus as a general transduction vector for mammalian cells," *Curr. Top Microbiol. Immunol.* 158:97–129, 1992.

Muzyczka and McLaughlin, "Use of adeno-associated virus as a mammalian transduction vector," In: *Current Communications in Molecular Biology: Viral Vectors*, Glzman and Hughes, Eds., Cold Spring Harbor Laboratory Press, Cold Spring Harbor, N.Y., pp. 39–44, 1988.

Nakai et al., "Adeno-associated viral vector-mediated gene transfer of human blood coagulation factor IX into mouse liver," *Blood* 91:4600–4607, 1998.

Nicolau and Gersonde, "Incorporation of inositol hexaphosphate into intact red blood cells, I. fusion of effector-containing lipid vesicles with erythrocytes," *Naturwissenschaften* (Germany), 66:563–566, 1979.

Nicolau and Sene, "Liposome-mediated DNA transfer in eukaryotic cells," *Biochem. Biophys. Acta* 721:185–190, 1982.

Parks, Melnick, Rongey, Mayor, "Physical assay and growth cycle studies of a defective adeno-satellite virus," *J. Virol.* 1:171–180, 1967.

Paterson et al., "The regions of the herpes simplex virus type 1 immediate early protein Vmw175 required for site specific DNA binding closely correspond to those involved in transcriptional regulation," *Nucleic Acids Res.* 16:11005–11025, 1988a.

Paterson et al., "Mutational dissection of the HSV-1 immediate-early protein Vmw175 involved in transcriptional transactivation and repression," *Virology* 166:186–196, 1988b.

Peel et al., "Efficient transduction of green fluorescent protein in spinal cord neurons using adeno-associated virus vectors containing cell type-specific promoters," *Gene Ther.* 4:16–24, 1997.

Pereira et al., "The adeno-associated virus (AAV) rep protein acts as both a repressor and an activator to regulate AAV transcription during a productive infection," *J. Virol.* 71:1079–1088, 1997.

Pikul et al., "In vitro killing of melanoma by liposome-delivered intracellular irradiation, *Arch. Surg.* 122:1417–1420, 1987.

Pinto-Alphandary et al., "A new method to isolate polyalkylcyanoacrylate nanoparticle preparations," *J. Drug Target* 3:167–169, 1995.

Potter et al., "Enhancer-dependent expression of human κ immunoglobulin genes introduced into mouse pre-B lymphocytes by electroporation," *Proc. Natl. Acad Sci. USA* 81:7161–7165, 1984.

Prokop and Bajpai, "Recombinant DNA Technology I," Conference on Progress in Recombinant DNA Technology Applications, Potosi, Mich., Jun. 3–8, 1990, *Ann. N.Y. Acad. Sci.* 646:1–383, 1991.

Quinlan et al., "The intranuclear location of a herpes simplex virus DNA binding protein is determined by the status of viral DNA replication," *Cell* 36:857–868, 1984.

Quintanar-Guerrero et al., "Preparation and characterization of nanocapsules from preformed polymers by a new process based on emulsification-diffusion techinque," *Phamr. Res.* 15:1056–1062, 1998.

*Remington's Pharmaceutical Sciences*, 15th Ed., Mack Publishing Company, 1975.

Renneisen et al., "Inhibition of expression of human immunodeficiency virus-1 in vitro by antibody-targeted liposomes containing antisense RNA to the env region," *J. Biol. Chem.* 265:16337–16342, 1990.

Rice and Knipe, "Genetic evidence for two distinct transactivation functions of the herpes simplex virus alpha protein ICP27," *J. Virol.* 64:1704–1715, 1990.

Ridgeway, "Mammalian expression vectors," In: *Vectors: A survey of molecular cloning vectors and their uses*, Rodriguez R L, Denhardt D T, ed., Stoneham: Butterworth, pp. 467–492, 1988.

Rippe et al., "DNA-mediated gene transfer into adult rat hepatocytes in primary culture," *Mol. Cell Biol.* 10:689–695, 1990.

Roizman and Sears, In: *Fields Virology*, (B. N. Fields, D. M. Knipe, P. Howley, R. M. Chanock, M. S. Hirsch, J. L. Melnick, T. P. Monath, and B. Roizman, eds.), Lippincott-Raven, Philadelphia, pp. 2231–2295, 1996.

Rose et al., "Evidence for a single-stranded adenovirus-associated virus genome: formation of a DNA density hybrid on release of viral DNA," *Proc. Natl. Acad. Sci. USA* 64:863–869, 1969.

Rose and Koczot, "Adenovirus-associated virus multiplication VII. Helper requirement for viral deoxyribonucleic acid and ribonucleic acid synthesis," *J. Virol.* 10:1–8, 1972.

Russell et al., "DNA synthesis and topoisomerase inhibitors increase transduction by adeno-associated virus vectors," *Proc. Natl. Acad. Sci. USA* 92:5719–5723, 1995.

Salvetti, "Factors influencing recombinant adeno-associated virus production," *Hum. Gene Ther.* 9:695–706, 1998.

Sambrook et al., *Molecular Cloning-A Laboratory Manual*, Cold Spring Harbor Laboratory Press, 1989.

Samulski et al., "Cloning of adeno-associated virus into pBR322: rescue of intact virus from the recombinant plasmid in human cells," *Proc. Natl. Acad. Sci. USA* 79:2077–2080, 1982.

Samulski and Shenk, "Adenovirus E1B 55-M, polypeptide facilitates timely cytoplasmic accumulation of adeno-associated virus mRNAs," *J. Virol.* 62:206–210, 1988.

Samulski et al., "A recombinant plasmid from which an infectious adeno-associated virus genome can be excised in vitro and its use to study viral replication," *J. Virol.* 61:3096–3101, 1987.

Samulski et al., "Rescue of adeno-associated virus from recombinant plasmids: gene correction within the terminal repeats of AAV," *Cell* 33:135–143, 1983.

Samulski et al., "Targeted integration of adeno-associated virus (AAV) into human chromosome 19," *EMBO J.* 10:3941–3950, 1991.

Sandri-Goldin and Mendoza, "A herpesvinis regulatory protein appears to act post-transcriptionally by affecting mRNA processing," *Genes Dev.* 6:848–863, 1992.

Sculier et al., "Pilot study of amphotericin B entrapped in sonicated liposomes in cancer patients with fungal infections," *J. Cancer Clin. Oncol.* 24:527–538, 1988.

Segal., "Biochemical Calculations" 2nd Edition, John Wiley & Sons, New York, 1976.

Shafron et al., "Reduced MK801 binding in neocortical neurons after AAV-mediated tansfections with NMDA-R1 antisense cDNA," *Brain Res.* 784:325–328, 1998.

Shepard et al., "Separation of primary structural components conferring autoregulation, transactivation, and DNA-binding properties to the herpes simplex virus transcriptional regulatory protein ICP4," *J. Virol.* 63:3714–3728, 1989.

Shepard et al., "A second-site revertant of a defective herpes simplex virus ICP4 protein with restored regulatory activities and impaired DNA-binding properties," *J. Virol.* 65:787–795, 1991.

Snyder, "Persistent and therapeutic concentrations of human factor IX in mice after hepatic gene transfer of recombinant AAV vectors," *Nat. Genet.* 16:270–276, 1997.

Song et al., "Sustained secretion of human alpha-1-antitrypsin from murine muscle transduced with adeno-associated virus vectors," *Proc. Natl. Acad. Sci. USA* 95: 14384–14388, 1998.

Srivastava et al., "Nucleotide sequence and organization of the adeno-associated virus 2 genome," *J. Virol.* 45:555–564, 1983.

Suzuki et al., "Direct gene transfer into rat liver cells by in vivo electroporation," *FEBS Lett.* 425:436–440, 1998.

Takakura, "Drug delivery systems in gene therapy," *Nippon Rinsho* 56:691–695, 1998.

Tamayose et al., "A new strategy for large-scale preparation of high-titer recombinant adeno-associated virus vectors by using packaging cell lines and sulfonated cellulose column chromatography," *Hum. Gene Ther.* 7:507–513, 1997.

Thomson and Efstathiou, "Acquisition of the human adeno-associated virus type-2 rep gene by human herpesvirus type-6," *Nature* 351:78–80, 1991.

Thomson et al., "Human herpesvirus 6 (HHV-6) is a helper virus for adeno-associated virus type 2 (AAV-2) and the AAV-2 rep gene homologue in HHV-6 can mediate AAV-2 DNA replication and regulate gene expression," *Virology* 204:304–311, 1994.

Tratschin et al., "Genetic analysis of adeno-associated virus: properties of deletion mutants constructed in vitro and evidence for an adeno-associated virus replication function," *J. Virol.* 51:611–619, 1984a.

Tratschin et al., "A human parvovirus, adeno-associated virus, as a eucaryotic vector: transient expression and encapsidation of the procaryotic gene for chloramphenicol acetyltransferase," *Mol. Cell. Biol.* 4:2072–2081, 1984b.

Tur-Kaspa et al., "Use of electroporation to introduce biologically active foreign genes into primary rat hepatocytes," *Mol. Cell Biol.* 6:716–718, 1986.

Vanbever et al., "In vivo noninvasive evaluation of hairless rat skin after high-voltage pulse exposure," *Skin Parmacol. Appl. Skin Physiol.* 11:23–34, 1998.

Vincent et al., "Analysis of recombinant adeno-associated virus packaging and requirements for rep and cap gene products," *J. Virol.* 71:1897–1905, 1997a.

Vincent et al., "Preclinical testing of recombinant adenoviral herpes simplex virus-thymidine kinase gene therapy for central nervous system malignancies," *Neurosurgery* 41:442–451, 1997b.

Vincent et al., "Replication and packaging of HIV envelope genes in a novel adeno-associated virus vector system," *Vaccine* 90:353–359, 1990.

Wagner et al., "Coupling of adenovirus to transferrin-polylysine/DNA complexes greatly enhances receptor-mediated gene delivery and expression of transfected genes," *Proc. Natl. Acad. Sci. USA* 89:6099–6103, 1992.

Wagner et al., "Efficient and persistent gene transfer of AAV-CFTR in maxillary sinus," *Lancet* 351:1702–1703, 1998.

Watson, "Fluid and electrolyte disorders in cardiovascular patients," *Nurs. Clin. North Am.* 22:797–803, 1987.

Weindler and Heilbronn, "A subset of herpes simplex virus replication genes provides helper functions for productive adeno-associated virus replication," *J. Virol.* 65:2476–2483, 1991.

Weitznan et al., "Interaction of wild-type and mutant adeno-associated virus (AAV) Rep proteins on AAV hairpin DNA," *J. Virol.* 70:2440–2448, 1996a.

Weitzman et al., "Recruitment of wild-type and recombinant adeno-associated virus into adenovirus replication centers," *J. Virol.* 70:1845–1854, 1996b.

Weller "Genetic analysis of HSV-1 gene required for genome replication," In: *Herpes virus transcription and its regulation,* Wagner Ed., Boca Raton, Fla.: CRC Press, pp. 105–136, 1991.

Wong et al., "Appearance of β-lactamase activity in animal cells upon liposome mediated gene transfer," *Gene* 10:87–94, 1980.

Wong and Neumann, "Electric field mediated gene transfer," *Biochim. Biophys. Res. Commun.* 107:584–587, 1982.

Wu and Wu, "Receptor-mediated in vitro gene transfections by a soluble DNA carrier system," *J. Biol. Chem.* 262:4429–4432, 1987.

Wu and Wu, "Evidence for targeted gene delivery to HepG2 hepatoma cells in vitro," *Biochemistry* 27:887–892, 1988.

Wu et al., "Identification of herpes simples virus type 1 genes required for origin-dependent DNA synthesis," *J. Virol.* 62:435, 1988.

Xiao et al., "Adeno-associated virus (AAV) vector antisense gene transfer in vivo decreases GABA(A) alpha1 containing receptors and increases inferior collicular seizure sensitivity," *Brain Res.* 756:76–83, 1997.

Xiao et al., "Efficient long-term gene transfer into muscle tissue of immunocompetent mice by adeno-associated virus vector," *J. Virol.* 70:8098–8108, 1996.

Xiao et al., "Production of high-titer recombinant adeno-associated virus vectors in the absence of helper adenovirus," *J. Virol.* 72:2224–2232, 1998.

Yang et al., "In vivo and in vitro gene transfer to mammalian somatic cells by particle bombardment," *Proc. Natl. Acad. Sci. USA* 87:9568–9572, 1990.

Zambaux et al., "Influence of experimental parameters on the characteristics of poly(lactic acid) nanoparticles prepared by a double emulsion method," *J. Controlled Release* 50:31–40, 1998.

Zhong and Hayward, "Assembly of complete functionally active herpes simplex virus DNA replication compartments and recruitment of associated viral and cellular proteins in transient cotransfection assays," *J. Virol.* 71:3146–3160, 1997.

Zolotukhin et al., "A 'humanized' green fluorescent protein cDNA adapted for high-level expression in mammalian cells," *J. Virol.* 70:4646–4654, 1996.

Zolotukhin et al., "Recombinant adeno-associated virus purification using novel methods improves infectious titer and yield," *Gene Ther.* 6:973–985, 1999.

zur Muhlen et al., "Solid lipid nanoparticles (SLN) for controlled drug delivery-drug release and release mechanism," *Eur. J. Pharm. Biopharm.* 45:149–155, 1998.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods, and in the steps or in the sequence of steps of the methods described herein, without departing from the concept, spirit and scope of the invention. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

What is claimed is:

1. A recombinant herpes simplex virus ICP27 deletion mutant, rHSV d27.1rc, deposited with the American Type Culture Collection as Accession Number PTA-4004.

2. A host cell that comprises the recombinant herpes simplex viral deletion mutant of claim 1.

3. The host cell of claim 2, wherein said cell is a mammalian cell.

4. The host cell of claim 3, wherein said mammalian cell is a human cell.

5. The host cell of claim 2, further comprising an rAAV vector or provirus.

6. The host cell of claim 5, wherein said rAAV vector or provirus comprises a therapeutic gene.

7. A composition comprising the recombinant herpes simplex viral deletion mutant of claim 1 or the host cell of claim 2.

8. The composition of claim 7, further comprising a pharmaceutical buffer or excipient.

* * * * *

UNITED STATES PATENT AND TRADEMARK OFFICE
CERTIFICATE OF CORRECTION

PATENT NO. : 6,783,972 B1
APPLICATION NO. : 09/404448
DATED : August 31, 2004
INVENTOR(S) : Barry J. Byrne et al.

It is certified that error appears in the above-identified patent and that said Letters Patent is hereby corrected as shown below:

On the Title Page, item [73]:

\*\*ASSIGNEE\*\*:   Please add the following additional Assignee:

THE JOHNS HOPKINS UNIVERSITY
BALTIMORE, MD (US)

Signed and Sealed this
Ninth Day of July, 2013

Teresa Stanek Rea
*Acting Director of the United States Patent and Trademark Office*

SEQUENCE LISTING

<160> NUMBER OF SEQ ID NOS: 4

<210> SEQ ID NO 1
<211> LENGTH: 24
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 1
atgagcaagg gcgaggaact gttc                                          24

<210> SEQ ID NO 2
<211> LENGTH: 24
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 2
tcacttgtac agctcgtcca tgcc                                          24

<210> SEQ ID NO 3
<211> LENGTH: 19
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 3
ctccatcact aggggttcc                                                19

<210> SEQ ID NO 4
<211> LENGTH: 24
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 4
cttcatcaca cagtactcca cggg                                          24